(12) United States Patent
Reddy et al.

(10) Patent No.: US 9,233,989 B2
(45) Date of Patent: Jan. 12, 2016

(54) SILA ANALOGS OF OXAZOLIDINONE DERIVATIVES AND SYNTHESIS THEREOF

(71) Applicant: Council of Scientific & Industrial Research, New Delhi (IN)

(72) Inventors: Dumbala Srinivasa Reddy, Pine (IN); Seetharam Singh Balamkundu, Pune (IN); Remya Ramesh, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/350,766

(22) PCT Filed: Oct. 11, 2012

(86) PCT No.: PCT/IB2012/055496
§ 371 (c)(1),
(2) Date: Apr. 9, 2014

(87) PCT Pub. No.: WO2013/054275
PCT Pub. Date: Apr. 18, 2013

(65) Prior Publication Data
US 2014/0296133 A1 Oct. 2, 2014

(30) Foreign Application Priority Data

Oct. 11, 2011 (IN) .......................... 2919/DEL/2011

(51) Int. Cl.
*C07D 231/00* (2006.01)
*A01N 37/18* (2006.01)
*C07F 7/10* (2006.01)
*C07F 7/08* (2006.01)
*A61K 31/695* (2006.01)
*A61K 45/06* (2006.01)

(52) U.S. Cl.
CPC ............... *C07F 7/10* (2013.01); *A61K 31/695* (2013.01); *A61K 45/06* (2013.01); *C07F 7/0816* (2013.01)

(58) Field of Classification Search
CPC ............................ C07F 7/0816; A61K 31/396
USPC ........................................... 514/2.9; 548/110
See application file for complete search history.

(56) References Cited

PUBLICATIONS

Ilg, Rainer; Burschka, Christian; Schepmann, Dirk; Wuensch, Bernhard; Tacke, Reinhold, Organometallics (2006), 25(22), 5396-5408.*
Gregory et al., "Antibacterials. Synthesis and structure-Activity Studies of 3-Aryl-2-oxooxazolidines. 2. The "A" Group", J Med Chem (Sep. 1990), 33(9):2569-2578.
Ilg et al., "Synthesis and Pharmacological Characterization of Sila-panamesine, a Sila-Analogue of the σ Receptor Ligand Panamesine", Organometallics (2006), 25(22):5396-5408.

* cited by examiner

*Primary Examiner* — Porfirio Nazario Gonzalez
*Assistant Examiner* — Kofi Adzamli
(74) *Attorney, Agent, or Firm* — Bret E. Field; Bozicevic, Field & Francis LLP

(57) ABSTRACT

The invention discloses silaanalogs of oxazolidinone compounds, to pharmaceutical compositions and to the synthesis of the oxazolidinone derivatives of formula I. The invention further relates to methods of treating a subject suffering with gram positive pathogens including those resistant to methicillin and vancomycin using the compound(s) or modulation of coagulation properties of blood-clotting cascade or compositions of the oxazolidinone derivatives of the invention.

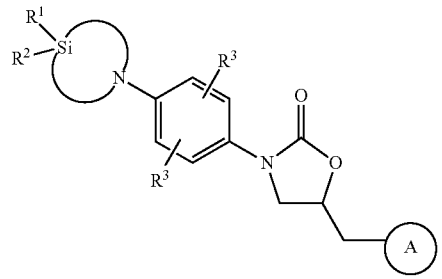

Formula I

8 Claims, No Drawings

SILA ANALOGS OF OXAZOLIDINONE DERIVATIVES AND SYNTHESIS THEREOF

FIELD OF THE INVENTION

This invention relates to novel oxazolidinone derivatives having potential antimicrobial activity over wide spectrum of pathogens and modulation of coagulation properties of blood-clotting cascade. More particularly, the invention relates to sila analogs of oxazolidinone compounds, to pharmaceutical compositions and to the synthesis of the oxazolidinone derivatives. The invention further relates to methods of treating a subject suffering with gram positive pathogens including those resistant to methicillin and vancomycin using the compound(s) or modulation of coagulation properties of blood-clotting cascade or compositions of the oxazolidinone derivatives of the invention.

BACKGROUND OF THE INVENTION AND THE PRIOR ART

Increased resistance of gram positive pathogens such as Staphylococcus aureus and Enterococcus faecium to conventional antibiotics led to the introduction new class of compounds with good activity. The oxazolidinone have a unique mechanism of action that is different from other antibiotics. The exact mechanism of antibacterial activity of oxazolidinone has not been established, but they appear to exert their inhibitory activity by interfering with an early step in protein synthesis in a generally bacteriostatic manner. Linezolid is the first antibiotic belonging to the new class of oxazolidinone compounds, developed in 1990s and first approved for use in 2000, it is the first commercially available 1,3-oxazolidinone antibiotic possessing excellent antibacterial activity against a wide variety of gram-positive pathogens including those resistant to methicillin and vancomycin. Linezolid is a synthetic oxazolidinone antimicrobial agent chemically designated as (S)—N-({3-[3-fluoro-4-(morpholin-4-yl)phenyl]-2-oxo-1,3-oxazolidin-5-yl}methyl)acetamide. Linezolid has demonstrated high in vitro antibacterial activity against Mycobacterium tuberculosis and has been used to treat complicated cases of resistant TB in several programmes. While the recommended use of linezolid is restricted to 28 days, with dosage at 600 mg twice daily, drug-resistant TB requires a much longer treatment duration (~2 years), and therefore, carries an increased risk of adverse effects. This drug suffers from poor pharmacokinetics which led to high dose, i.e., twice daily. Also there are several cases of developing linezolid resistance. By this silicon-switch approach, one can expect to improve pharmacokinetic properties which in turn may reduce the dose of the drug. More importantly, the problem of resistance development can be addressed as there is a structural difference in new sila analogs.

As of 2009, linezolid is the only marketed oxazolidinone, although others are in the process of development. As a protein synthesis inhibitor, it stops the growth of bacteria by disrupting their production of proteins. Linezolid targets ribosomes, inhibits the initiation step of protein synthesis by preventing the formation of functional 70S initiation complex, which is essential to the bacterial translation process and kills bacteria. Linezolid is used for the treatment of vancomycin-resistant Enterococcus faecium, including cases with concurrent bacteremia, treatment of nosocomial pneumonia, complicated and uncomplicated skin and skin structure infections (including diabetic foot infections without concomitant osteomyelitis) and community-acquired pneumonia caused by susceptible strains of specific organisms. Although bacterial resistance to linezolid has remained very low since it was first detected in 1999, however, the world wide reports on development of resistance to linezolid are constantly increasing.

Structurally related PNU-100480 is currently being developed for the treatment of both drug resistant and sensitive tuberculosis (TB).

Another related compound rivaroxaban (BAY 59-7939) is an oxazolidinone derivative optimized for inhibiting both free Factor Xa and Factor Xa bound in the prothrombinase complex. It is a highly selective direct Factor Xa inhibitor with oral bioavailability and rapid onset of action Inhibition of Factor Xa interrupts the intrinsic and extrinsic pathway of the blood coagulation cascade, inhibiting both thrombin formation and development of thrombi. Rivaroxaban has predictable pharmacokinetics across a wide spectrum of patients.

Therefore, it is necessary to develop an effective alternative belonging to the oxazolidinone group of compounds having activity against a wide variety of gram-positive pathogens including those resistant to methicillin and vancomycin as the oxazolidinones are proved to be effective in inhibiting bacterial translation process than the existing ones. The compounds of the present invention are useful antimicrobial agents, effective against a number of human and veterinary pathogens, including gram-positive aerobic bacteria such as Staphylococci, Streptococci and Enterococci as well as anaerobic organisms such as Bacteroides spp. and Clostridia spp. and acid-fast organisms such as Mycobacterium tuberculosis, Mycobacterium avium and Mycobacterium spp. The compounds of the present invention are also useful in modulation of coagulation properties of blood-clotting cascade.

OBJECTIVE OF THE INVENTION

The objective of the invention is to provide novel oxazolidinone derivatives having potential antimicrobial activity over wide spectrum of pathogens useful for treating variety of bacterial infections including tuberculosis or useful for treating cardiovascular related problems.

SUMMARY OF THE INVENTION

Accordingly, one of the embodiments of the present invention is to provide sila analogs of oxazolidinone derivatives of formula I as shown below:

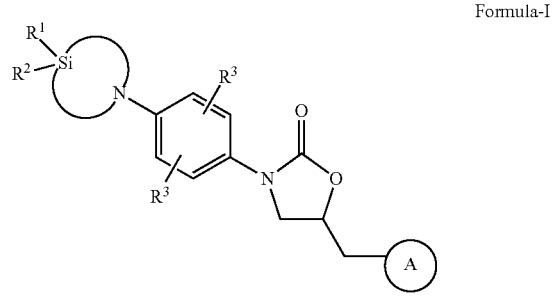

Formula-I wherein, $R^1$ and $R^2$ each are individually selected from C1 to C12 alkyl, aryl, heteroaryl, aralkyl or $R^1$ and $R^2$ may form 4-8 membered alicyclic or aromatic ring with additionally containing hetero atom;

$R^3$ is selected from hydrogen, chloro, fluoro, nitro, cyano, amino, C1-C8 alkyl amino, C1-C8 dialkyl amino, C1-C8 alkoxy, p-toluenesulfonyl, $CONH_2$, NHCOR, COOH, $CF_3$, hydroxy, OCOR, alkyl(optionally substituted with chloro, fluoro, hydroxy, C1-C8 alkoxy, amino, C1-C8 alkylamino, or C1-C8 dialkylamino), aryl, hetero aryl, aralkyl and, "A" is independently selected from the group consisting of;

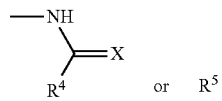

wherein, $R^4$ is selected from hydrogen, (C1-C8) alkyl optionally substituted with chloro, fluoro, hydroxy, C1-C8 alkoxy, amino, C1-C8 alkylamino, or C1-C8 dialkylamino, aryl, hetero aryl, or aralkyl;

X is selected from O, S, NH, or N—OR';

R' is selected from C1 to C12 alkyl, aryl, heteroaryl, aralkyl and;

$R^5$ is selected from hydrogen, hydroxyl, (C1-C4) alkyl, alkyl optionally substituted with chloro, fluoro, hydroxyl, C1-C8 alkoxy, amino, C1-C8 alkylamino, or C1-C8 dialkylamino, aryl, hetero aryl, aralkyl; p-toluenesulfonyl, methanesulfonyl, $N_3$.

Another embodiment of the present invention is that the said compound is found to have antibacterial activity against strains of *S. aureus, S. epidermidis, E. faecalis, E. faecium* and *E. coli*.

Still another embodiment of the present invention is that the said compound is found to have anti tubercular activity against strain of *Mycobacterium tuberculosis* $H_{37}Rv$.

Still another embodiment of the present invention is the process for synthesis of sila analogs of oxazolidine derivatives comprising of i. reacting 1,4-azasilinane hydrochloride compound of general formula (a)

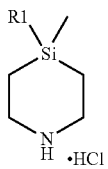

wherein R1 is alkyl or phenyl with fluronitrophenyl in presence of triethylamine in ethyl acetate at a temperature ranging between 20-45° C. to obtain N-aryl-1,4-azasilinane compound of general formula (b) wherein R is alkyl or phenyl, one or two R2 wherein R2 is F or H

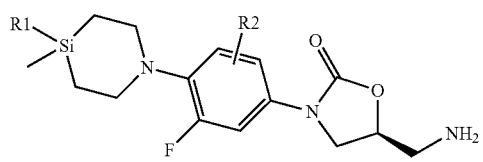

ii reacting compound (b) with $H_2$—Pd/C in THF at a pressure of 35-50 psi to obtain an amino compound, filtrating the reaction mixture through celite, followed by addition of CBzCl to the filtrate and stirring for 5 hours at room temperature to obtain compound of general formula (c) Benzyl 4-(4,4-dimethyl-1,4-azasilinan-1-yl)-3-fluorophenylcarbamate wherein R1 is alkyl or phenyl, wherein R2 is F or H

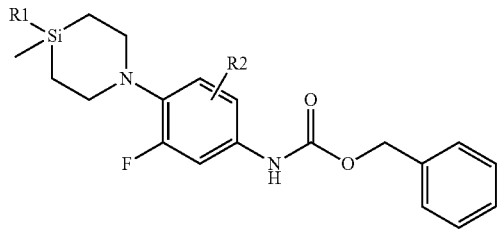

iii reacting compound (c) with (S)-tert-butyl 3-chloro-2-hydroxypropylcarbamate in LiO'Bu at a temperature in the range of 0° C. to 25° C. to obtain compound of general formula (d) (S)-5-(aminomethyl)-3-(4-(4,4-dimethyl-1,4-azasilinan-1-yl)-3-fluorophenyl)oxazolidin-2-one wherein R is alkyl or phenyl, wherein R2 is F or H

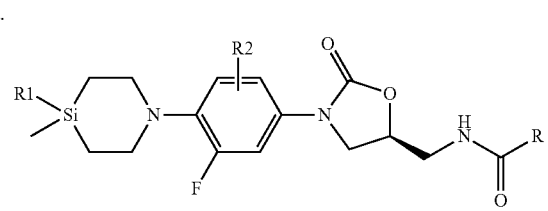

iv reacting compound (d) with acid chloride of formula RCOCl wherein R is alkyl and N,N-diisopropylethylamine (DIPEA) to obtain corresponding amide compounds, a.

v converting compound (d) to corresponding ester of compound 14 (S)-methyl((3-(4-(4,4-dimethyl-1,4-azasilinan-1-yl)-3-fluorophenyl)-2-oxooxazolidin-5-yl)methyl)carbamate by reacting with Carbonyl diimidazole (CDI) and trimethylamine in the presence of methanol, vi converting compound (d) to compound of formula 15 (S)—O-methyl((3-(4-(4,4-dimethyl-1,4-azasilinan-1-yl)-3-fluorophenyl)-2-oxooxazolidin-5-yl)methyl)carbamothioate by reacting with $CSCl_2$ in the presence of methanol to obtain compound of formula 15.

Still another embodiment of the present invention is the process for the synthesis of compound 17 to 21 comprising of the following steps:—

(i) reacting compound of general formula (c) with compound 16 glycidylbutyrate in the presence of n-BuLi in THF at a temperature of about 25° C. to obtain compound of formula 17 (R)-3-(4-(4,4-dimethyl-1,4-azasilinan-1-yl)-3-fluorophenyl)-5-(hydroxymethyl)oxazolidin-2-one.

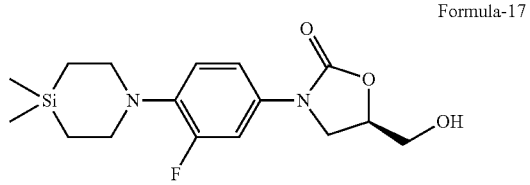

Formula-17

(ii) converting the hydroxycompound 17 to corresponding misilate by reacting with Methanesulfonylchloride in the presence of trimethylamine followed by diazotization to produce azido compound of formula 19 (R)-5-(azidomethyl)-3-(4-(4,4-dimethyl-1,4-azasilinan-1-yl)-3-fluorophenyl)oxazolidin-2-one

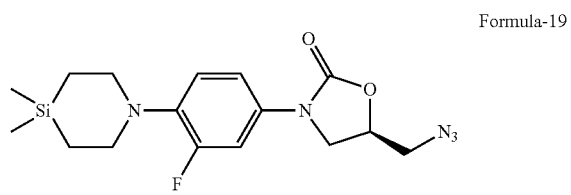 [SMILES: C[Si]1(C)CCN(c2ccc(N3C[C@H](CN=[N+]=[N-])OC3=O)cc2F)CC1]

Formula-19

(iii) reacting azido compound 19 with bicyclodiene under reflux temperature to produce compound of formula 21 (R)-5-((1H-1,2,3-triazol-1-yl)methyl)-3-(4-(4,4-dimethyl-1,4-azasilinan-1-yl)-3-fluorophenyl)oxazolidin-2-one

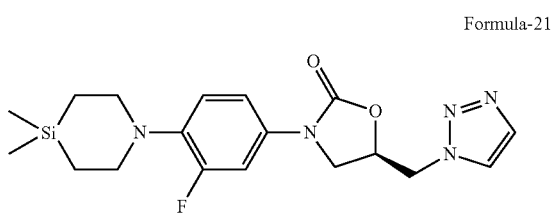 [SMILES: C[Si]1(C)CCN(c2ccc(N3C[C@H](Cn4ccnn4)OC3=O)cc2F)CC1]

Formula-21

Yet another embodiment of the present invention is to provide pharmaceutical compositions comprising novel class of compounds of formula I with one or more pharmaceutical carriers.

Yet another embodiment of the present invention is to provide methods of treating or preventing microbial infections in a subject comprising administering an effective amount of compounds of formula I according to the invention together with one or more pharmaceutical carriers.

Yet another embodiment of the present invention is to provide use of compounds of formula I according to the invention for the preparation of medicaments useful for treating or preventing microbial infections in a subject.

DETAILED DESCRIPTION OF THE INVENTION

In light of the continuous need in the art, the current inventors have designed novel oxazolidinones compounds with a view to provide an effective alternate oxazolidinone compound with more target specificity over linezolid, rivaroxaban, or PNU-100480, to overcome the problem of linezolid drug resistance or modulation of Pharmacokinetic (PK) properties.

Accordingly, the instant invention provides sila analogs of oxazolidinone derivatives of formula I as shown below:

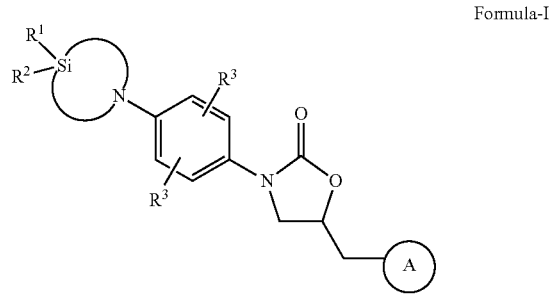

Formula-I wherein, $R^1$ and $R^2$ each are individually selected from C1 to C12 alkyl, aryl, heteroaryl, aralkyl or $R^1$ and $R^2$ may form 4-8 membered alicyclic or aromatic ring with additionally containing hetero atom;

$R^3$ is selected from hydrogen, chloro, fluoro, nitro, cyano, amino, C1-C8 alkyl amino, C1-C8 dialkyl amino, C1-C8 alkoxy, p-toluenesulfonyl, $CONH_2$, NHCOR, COOH, $CF_3$, hydroxy, OCOR, alkyl(optionally substituted with chloro, fluoro, hydroxy, C1-C8 alkoxy, amino, C1-C8 alkylamino, or C1-C8 dialkylamino), aryl, hetero aryl, aralkyl and, "A" is independently selected from the group consisting of;

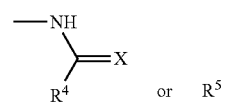

or $R^5$ wherein, $R^4$ is selected from hydrogen, (C1-C8) alkyl optionally substituted with chloro, fluoro, hydroxy, C1-C8 alkoxy, amino, C1-C8 alkylamino, or C1-C8 dialkylamino, aryl, hetero aryl, or aralkyl;

X is selected from O, S, NH, or N—OR';

R' is selected from C1 to C12 alkyl, aryl, heteroaryl, aralkyl and;

$R^5$ is selected from hydrogen, hydroxyl, (C1-C4) alkyl, alkyl optionally substituted with chloro, fluoro, hydroxyl, C1-C8 alkoxy, amino, C1-C8 alkylamino, or C1-C8 dialkylamino, aryl, hetero aryl, aralkyl; p-toluenesulfonyl, methanesulfonyl, $N_3$ The compounds of formula I according to the invention encompass an enantiomer, diastereomer, racemate, tautomer, geometrical isomer, or pharmaceutically acceptable salt thereof.

The compound of formula I according to the present invention also encompasses esters and pure forms thereof.

Accordingly, in a further embodiment, the invention encompasses novel compounds of formula I as below (S)—N-((3-(4-(4,4-dimethyl-1,4-azasilinan-1-yl)-3-fluorophenyl)-2-oxooxazolidin-5-yl)methyl)acetamide ((12): (NDS 10024))

(S)-5-(aminomethyl)-3-(4-(4,4-dimethyl-1,4-azasilinan-1-yl)-3-fluorophenyl)oxazolidin-2-one11: (NDS-10057)

(S)—N-((3-(4-(4,4-dimethyl-1,4-azasilinan-1-yl)-3-fluorophenyl)-2-oxooxazolidin-5-yl)ethyl)propionamide (13): (NDS 10033):)

(S)-methyl((3-(4-(4,4-dimethyl-1,4-azasilinan-1-yl)-3-fluorophenyl)-2-oxooxazolidin-5-yl)methyl)carbamate(14): (NDS-10061)

(S)—O-methyl((3-(4-(4,4-dimethyl-1,4-azasilinan-1-yl)-3-fluorophenyl)-2-oxooxazolidin-5-yl)methyl)carbamothioate (15):(NDS-10062)

(R)-3-(4-(4,4-dimethyl-1,4-azasilinan-1-yl)-3-fluorophenyl)-5-(hydroxymethyl)oxazolidin-2-one (17): (NDS-10059)

(R)-5-((1H-1,2,3-triazol-1-yl)methyl)-3-(4-(4,4-dimethyl-1,4-azasilinan-1-yl)-3-fluorophenyl)oxazolidin-2-one (21) (NDS-10060):

(S)-5-(aminomethyl)-3-(4-(4,4-dimethyl-1,4-azasilinan-1-yl)-3,5-difluorophenyl)oxazolidin-2-one (22): (NDS-10054)

(S)—N-((3-(4-(4,4-dimethyl-1,4-azasilinan-1-yl)-3,5-difluorophenyl)-2-oxooxazolidin-5-yl)methyl)acetamide (23): (NDS-10028)

(S)—N-((3-(4-(4,4-dimethyl-1,4-azasilinan-1-yl)-3,5-difluorophenyl)-2-oxooxazolidin-5-yl)methyl)propionamide (24): (NDS-10056)

(S)-methyl(3-(4-(4,4-dimethyl-1,4-azasilinan-1-yl)-3,5-difluorophenyl)-2-oxooxazolidin-5-yl)methylcarbamate (25): (NDS-10053)

(S)—O-methyl(3-(4-(4,4-dimethyl-1,4-azasilinan-1-yl)-3,5-difluorophenyl)-2-oxooxazolidin-5-yl)methylcarbamothioate (26): (NDS-10055)

(R)-3-(4-(4,4-dimethyl-1,4-azasilinan-1-yl)-3,5-difluorophenyl)-5-(hydroxymethyl)oxazolidin-2-one (27): (NDS-10052)

(R)-5-((1H-1,2,3-triazol-1-yl)methyl)-3-(4-(4,4-dimethyl-1,4-azasilinan-1-yl)-3,5-difluorophenyl)oxazolidin-2-one (28): (NDS-10058)

(S)-5-(aminomethyl)-3-(3,5-difluoro-4-(4-methyl-4-phenyl-1,4-azasilinan-1-yl)phenyl)oxazolidin-2-one (29): (NDS-10070))

(S)—N-((3-(3,5-difluoro-4-(4-methyl-4-phenyl-1,4-azasilinan-1-yl)phenyl)-2-oxooxazolidin-5-yl)methyl)acetamide (30):(NDS-10068)

(S)—N-((3-(3,5-difluoro-4-(4-methyl-4-phenyl-1,4-azasilinan-1-yl)phenyl)-2-oxooxazolidin-5-yl)methyl)propionamide (31):(NDS-10069)

(R)-3-(3,5-difluoro-4-(4-methyl-4-phenyl-1,4-azasilinan-1-yl)phenyl)-5-(hydroxymethyl)oxazolidin-2-one(32): (NDS-10071).

Thus, silicon analogs of oxazolidinone derivatives of formula I, with silicon in the ring, being more electropositive and highly lipophilic in nature may have effective binding by increased avidity to the target site; as a result, one would be able to get better therapeutic effectiveness at a significantly lower dose, hence minimizing the toxicity associated with dose duping and may also possibly delay the drug resistance. It is also expected to alter the pharmacokinetics of the drug in a favorable manner.

In another preferred embodiment, the invention provides pharmaceutically acceptable salts of the compounds of the formula (I) for example organic or inorganic salts. The pharmaceutically acceptable acid(s) and base addition salts of compounds of general formula (I) encompasses wide variety of organic and inorganic acids and bases and include but not limited to the physiologically acceptable salts which are often used in pharmaceutical industry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalandioic acids, aromatic acids, aliphatic and aromatic sulfonic acids may also be used. Such pharmaceutically acceptable salts thus include acetate, phenylacetate, trifluoroacetate, ascorbate, benzoate, hydroxybenzoate, methoxybenzoate, methylbenzoate, cinnamate, citrate, formate, fumarate, glycollate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, sulfate, bisulfate, pyrosulfate, sulfite, bisulfite, sulfonate, benzenesulfonate, ethanesulfonate, 2-hydroxyethanesulfonate, methanesulfonate, p-toluenesulfonate, tartrate and the like.

In another preferred embodiment, the invention provides pharmaceutical compositions comprising a compound selected from the formula (I) optionally further comprise at least one pharmaceutically acceptable excipient, carrier, or diluent. The pharmaceutical compositions may optionally comprise, in addition to a compound selected from the formula (I), one or more suitable anti-bacterial drugs such as vancomycin, doxycycline, penicillin, clindamycin, gentamicin, rifampicin etc. to provide synergistic effect on treatment regimen.

The pharmaceutical compositions of the present invention may be in any form which allows for the composition to be administered to a subject. For example, the composition may be in the form of a solid, liquid or gas (aerosol). Typical routes of administration include, without limitation, topical, parenteral, transdermal, intraperitoneal (IP), intravenous (IV), oral (PO), intramuscular (IM), intracutaneous (IC), intradermal (ID), intrauterine and intrarectal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a subject.

The solid dosage form may be formulated as tablets, pellets, capsules having different release pattern such as immediate, sustained, controlled, modified and delayed release profiles. The dosage forms may be prepared in conventional manner using specific excipients to achieve desired dosage form and release profile. It will be obvious to those of ordinary skill in the art that the optimal dosage of the active ingredient(s) in the pharmaceutical composition(s) will depend on a variety of factors including the type of subject, the particular form of the active ingredient, the manner of administration, severity of the infection/disease and the dosage form employed. Generally, the quantity of active compound will range between 0.5% to 90% by weight of the composition. Normally, the effective amount of dosage of antibacterial active component will be in the range of about 0.1 to about 100 mg/kg, more preferably about 3.0 to about 50 mg/kg of body weight/day.

In a further embodiment, the invention provides method of inhibiting a bacterial infection in a mammal, comprising administering to the said mammal in need thereof en effective amount of compound of formula I. The quantity of the compound of formula I used in pharmaceutical compositions of the present invention will vary depending upon the body weight of the patient and the mode of administration and can be of any effective amount to achieve the desired therapeutic effect. The compound of the present invention can also be administered optionally with other actives depending on the disease conditions.

One preferred silicon analog of oxazolidinone derivatives of formula I, designated herein after as formula 12 according to the present invention is as shown below:

Formula 12

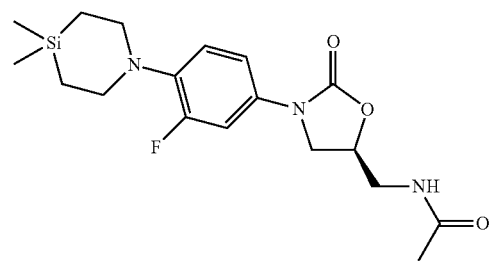

Compound of formula 12 according to the present invention may be prepared as per the scheme 1 provided below:

Scheme 1:
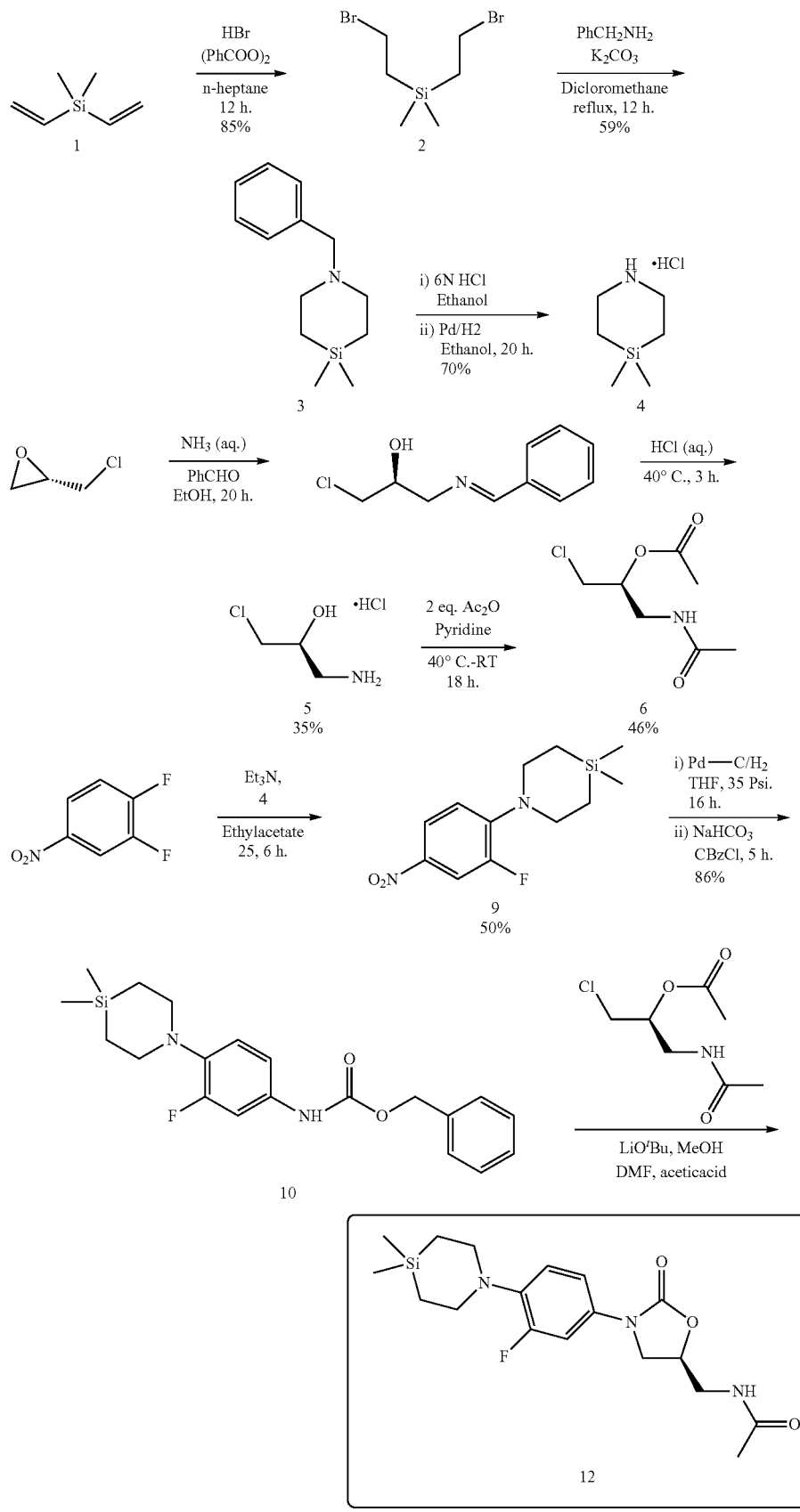

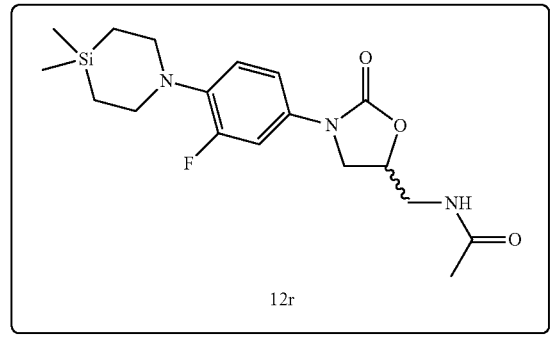

12r

Compound 12r was prepared following similar procedure as scheme 1 starting from racemic epichlorohydrin.

Another preferred sila analog of oxazolidinone derivatives of formula I, designated herein after as formula 11 according to the present invention is as shown below:

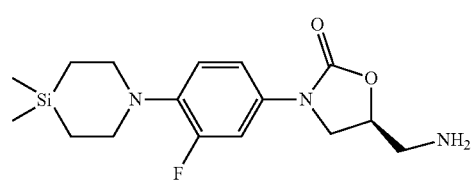

Formula 11

Compound of formula 11 according to the present invention may be prepared as per the scheme 2 provided below:

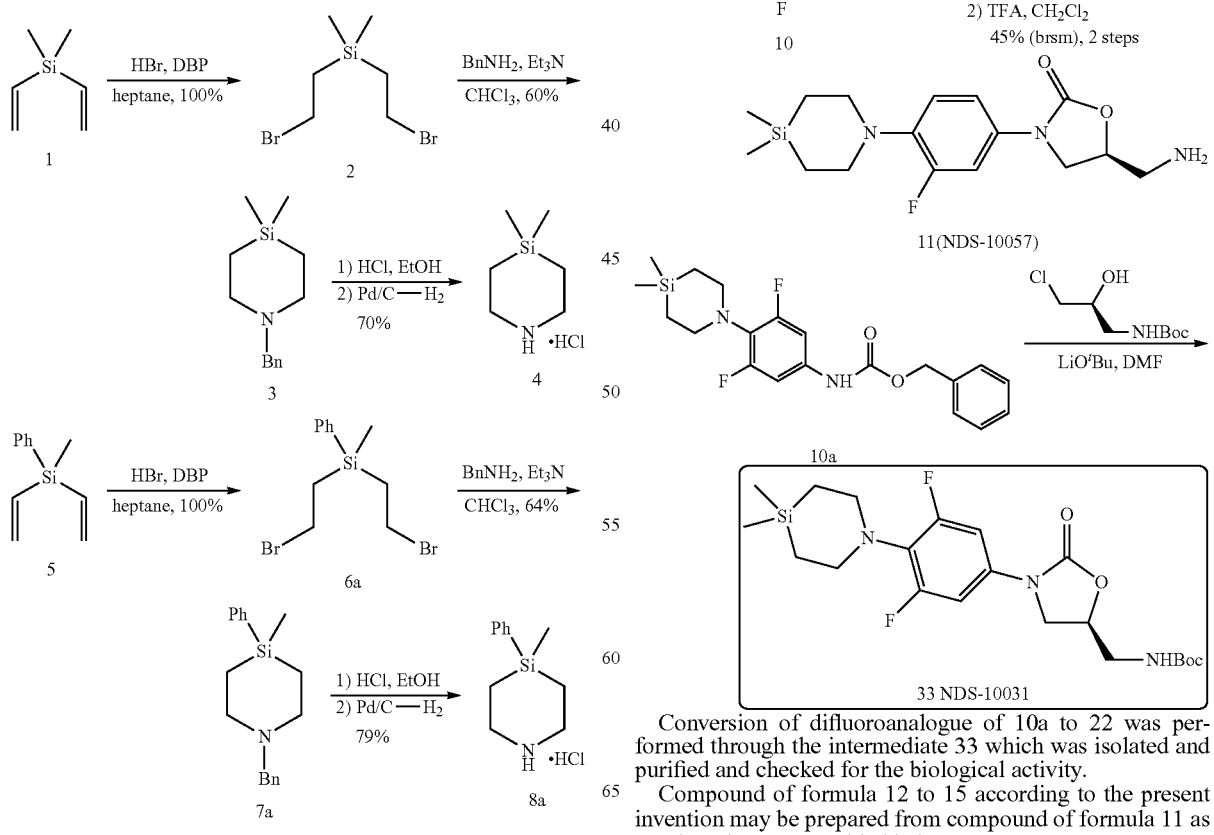

Conversion of difluoroanalogue of 10a to 22 was performed through the intermediate 33 which was isolated and purified and checked for the biological activity.

Compound of formula 12 to 15 according to the present invention may be prepared from compound of formula 11 as per the scheme 3 provided below:

Scheme 3

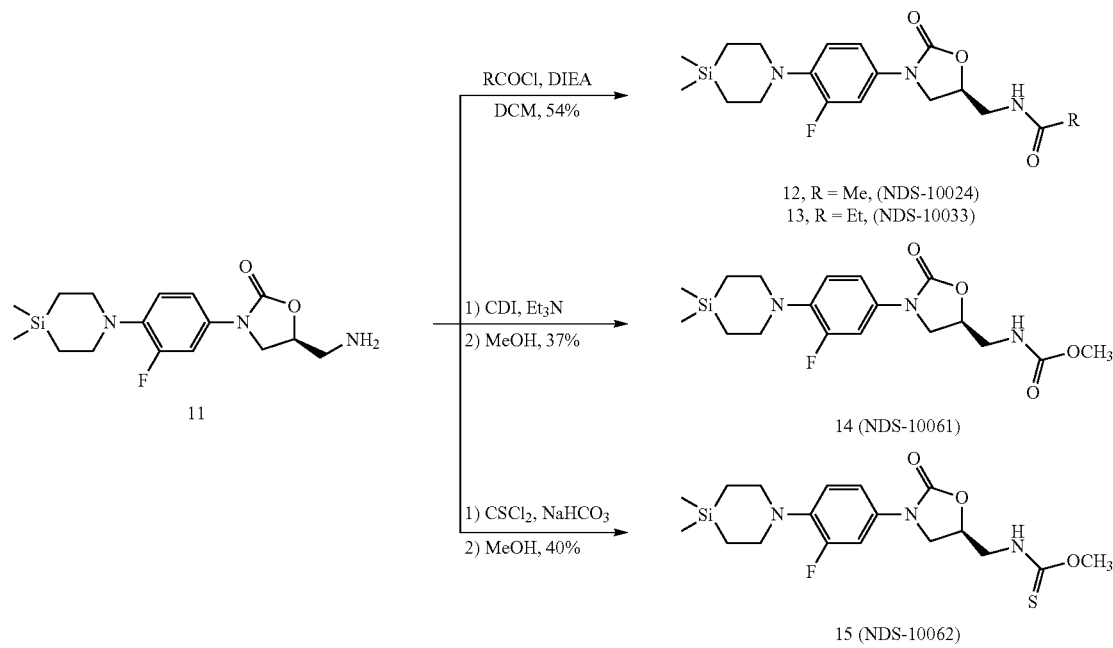

In yet another preferred embodiment, compounds of formula 17, 19 and 21 are prepared as per the following scheme 4.

Scheme 4

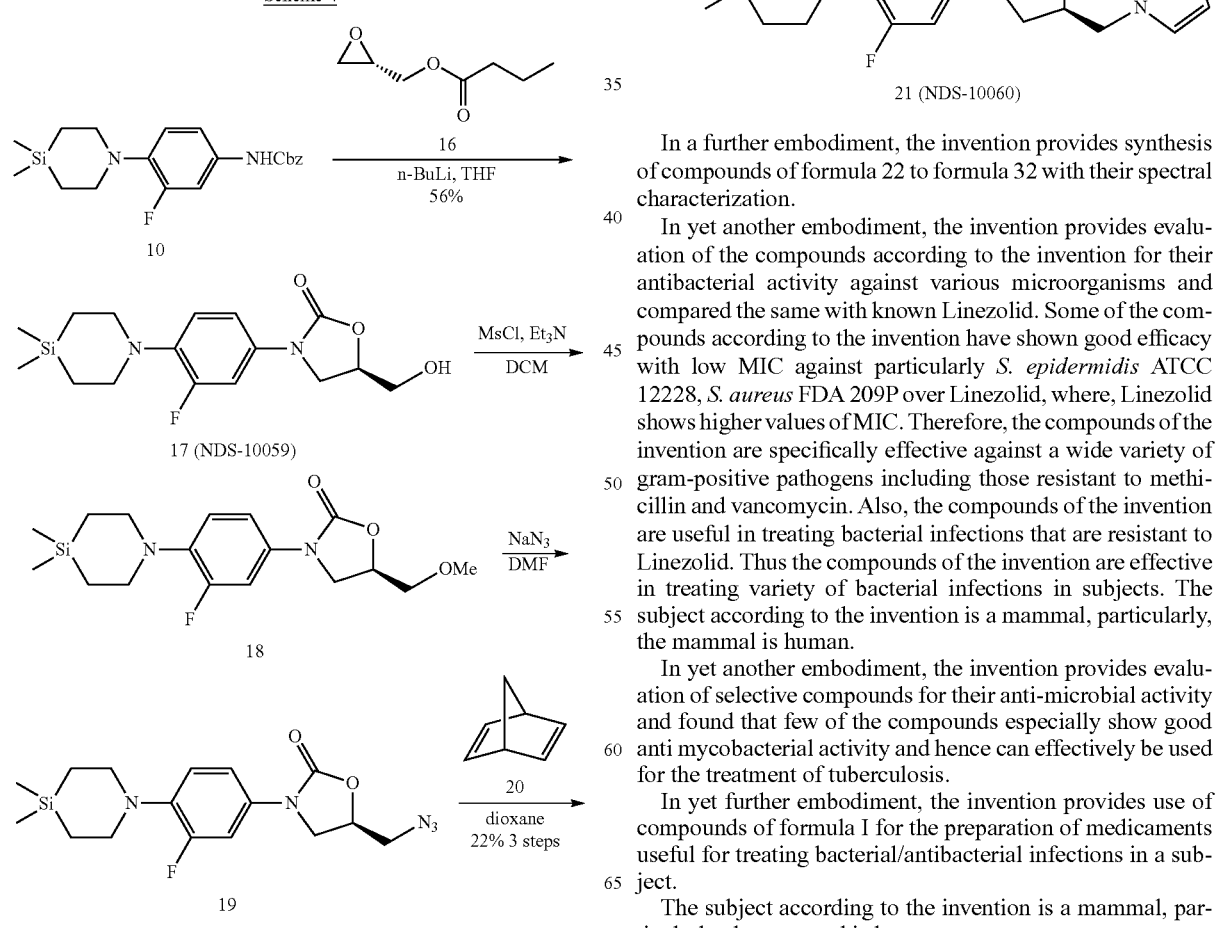

-continued 21 (NDS-10060)

In a further embodiment, the invention provides synthesis of compounds of formula 22 to formula 32 with their spectral characterization.

In yet another embodiment, the invention provides evaluation of the compounds according to the invention for their antibacterial activity against various microorganisms and compared the same with known Linezolid. Some of the compounds according to the invention have shown good efficacy with low MIC against particularly S. epidermidis ATCC 12228, S. aureus FDA 209P over Linezolid, where, Linezolid shows higher values of MIC. Therefore, the compounds of the invention are specifically effective against a wide variety of gram-positive pathogens including those resistant to methicillin and vancomycin. Also, the compounds of the invention are useful in treating bacterial infections that are resistant to Linezolid. Thus the compounds of the invention are effective in treating variety of bacterial infections in subjects. The subject according to the invention is a mammal, particularly, the mammal is human.

In yet another embodiment, the invention provides evaluation of selective compounds for their anti-microbial activity and found that few of the compounds especially show good anti mycobacterial activity and hence can effectively be used for the treatment of tuberculosis.

In yet further embodiment, the invention provides use of compounds of formula I for the preparation of medicaments useful for treating bacterial/antibacterial infections in a subject.

The subject according to the invention is a mammal, particularly, the mammal is human.

EXAMPLES

The following examples, which include preferred embodiments, will serve to illustrate the practice of this invention, it being understood that the particulars shown are by way of example and for purpose of illustrative discussion of preferred embodiments of the invention.

Preparation of (S)—N-(2-(chloromethyl)-4-oxopentyl)acetamide (6) (as per scheme 1)

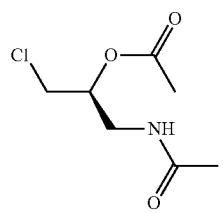

The compound (S)—N-(2-(chloromethyl)-4-oxopentyl) acetamide was prepared from (S)-epichlorohydrin according to the literature procedure with an isolated yield of 30% in 3 steps. (Perrault, W. R.; Pearlman, B. A.; Godrej, D. B.; Jeganathan, A.; Yamagata, K.; Chen, J. J.; Lu, C. V.; Herrinton, P. M.; Gadwood, R. C.; Chan, L.; Lyster, M. A.; Maloney, M. T.; Moeslein, J. A.; Greene, M. L.; Barbachyn, M. R. *Org. Pro. Res. and Development.* 2003, 7, 533-546).

Preparation of 1-benzyl-4,4-dimethyl-1,4-azasilinane (3)

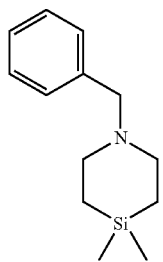

Benzylamine (17.56 g, 0.16 mol) and $K_2CO_3$ (3.4 g, 24.6 mmol) are added to a solution of bis(2-bromoethyl)dimethylsilane 2(4.0 g, 16.4 mmol) in Dichloromethane (DCM). The mixture is then refluxed for 16 h. Water is added and the aqueous layer is extracted with DCM. It is then washed with 5% sodiumhydroxide (NaOH) solution, dried and concentrated. The product is purified by column chromatography on silica using hexane-ethylacetate mixtures to obtain the product as a colorless liquid 3 (2.1 g) in 59% yield.

$^1$H NMR (200 MHz, CDCl3): δ 7.28-7.22 (m, 5H), 3.51 (s, 2H), 2.64 (t, J=6.33 Hz, 4H), 0.71 (t, J=6.44 Hz, 4H), 0.00 (s, 6H).

Preparation of 4,4-dimethyl-1,4-azasilinane hydrochloride (4)

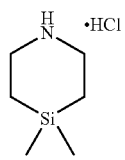

To a solution of 3 (2.3 g, 10.5 mmol) in ethanol (EtOH), 6 N HCl (10.5 mmol) is added and the solvent is removed under reduced pressure. The reaction mixture is co-evaporated with EtOH (2×10 mL) and recrystallized from EtOH-diethyl ether. To a slurry of Pd/C in EtOH, an ethanolic solution of the HCl salt is added dropwise and stirred at 25° C. under hydrogen atmosphere for 20 h. The reaction mixture is filtered through celite, washed with 2×20 mL of Methanol. The filtrate is concentrated under reduced pressure to give a viscous oil which is titrated with diethyl ether to obtain the product 4 as a white solid (950 mg) in 70% yield. This compound was previously documented in WO 2006/066872.

Preparation of 1-(2-fluoro-4-nitrophenyl)-4,4-dimethyl-1,4-azasilinane (9)

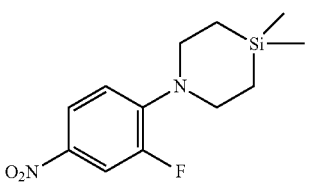 [SMILES: C[Si]1(C)CCN(c2ccc([N+](=O)[O-])cc2F)CC1]

To a solution of 4 (500 mg, 3.85 mmol) in ethylacetate, triethylamine (973 mg, 9.63 mmol) is added and stirred at 25° C. for 10 min. The reaction mixture is cooled to 0° C. and 3,4-difluoronitrobenzene (612 mg, 3.85 mmol) is added dropwise and allowed to stir at 25° C. for 6 h. Water is then added and the organic layer is separated. The aqueous layer is extracted with EtOAc and the solvent is removed. The product is purified by column chromatography using hexanes-EtOAc mixtures to obtain the product as a crystalline yellow solid 9 (721 mg) in 70% isolated yield.

$^1$H NMR (50 MHz, CDCl$_3$): δ 7.93-7.84 (m, 2H), 6.86 (t, J=4 Hz, 1H), 3.70-3.67 (m, 4H), 0.91-0.85 (m, 4H), 0.12 (s, 6H). $^{13}$C NMR (100 MHz, CDCl$_3$): δ 151.12 (d, J=246.71 Hz), 144.43 (d, J=7.13 Hz), 137.84 (d, J=8.59 Hz), 121.45, 115.90 (d, J=4.61 Hz), 113.18 (J=27.78 Hz), 49.44, 13.79, −2.85.

Preparation of Benzyl 4-(4,4-dimethyl-1,4-azasilinan-1-yl)-3-fluorophenylcarbamate (10)

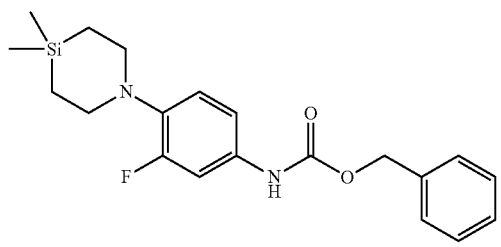 [SMILES: C[Si]1(C)CCN(c2ccc(NC(=O)OCc3ccccc3)cc2F)CC1]

To a solution of 9 (610 mg, 2.28 mmol) in Tetrahydrofuran (THF) Pd/C is added for hydrogenation under a pressure of 35 psi in a par hydrogenator. The reaction mixture is filtered through celite. To the filtrate, saturated NaHCO$_3$ (420 mg, 5.01 mmol), CBzCl (427 mg, 2.5 mmol) are added and stirred at 25° C. for 5 h. The solvent is removed, 10 mL water is added and the aqueous layer is extracted with EtOAc. The crude mixture is then subjected to column chromatography on silica gel using hexane-DCM mixtures to afford the product 10 as a viscous liquid (690 mg) in 82% yield.

$^1$H NMR (400 MHz, CDCl$_3$): δ 7.41-7.37 (m, 5H), 6.94-6.93 (m, 2H), 6.68 (s, 1H), 5.21 (s, 1H), 3.3 (t, J=6.38 Hz, 4H), 0.93 (t, J=6.08 Hz, 4H), −0.13 (s, 6H).

Preparation of (S)—N((3-(4-(4,4-dimethyl-1,4-azasilinan-1-yl)-3-fluorophenyl)-2 oxooxazolidin-5-yl)methyl)acetamide (12)

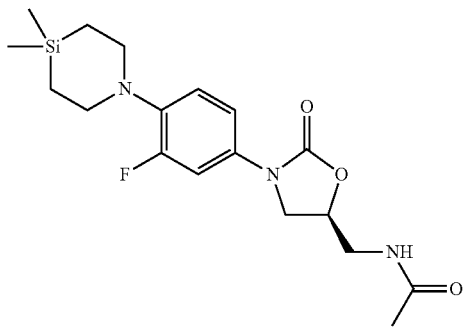 [SMILES: CC(=O)NC[C@H]1CN(c2ccc(N3CC[Si](C)(C)CC3)c(F)c2)C(=O)O1]

To a solution of 8 (50 mg, 0.135 mmol) in dimethylformamide (DMF), lithium-t-butoxide (LiO$^t$Bu) (32.3 mg, 0.4 mmol) is added. The mixture is stirred at 25° C. for 15 min, followed by the addition of MeOH (0.01 mL, 0.27 mmol). 6 (52 mg, 0.27 mmol) is then added and the reaction mixture is allowed to stir at 25° C. for 24 h. Glacial acetic acid is then added and the organic phase is extracted with EtOAc and washed with brine solution. The crude material is purified by column chromatography on silica gel using hexane-EtOAC mixtures to furnish the pure product 12. The analogous procedure for the corresponding morpholine analogue was adapted from Lu, C. V.; Chen, J. J.; Perrault, W. R.; Conway, B. G.; Maloney, M. T.; Wang, Y. Org. Pro. Res. and Development. 2006, 10, 272-277.

$^1$H NMR (200 MHz, CDCl$_3$): δ 7.33 (d, J=13.8 Hz, 1H), 7.02-6.94 (m, 2H), 6.52 (t, J=5.8 Hz, 1H), 4.77-4.73 (m, 1H), 3.99 (t, J=9.04 Hz, 1H), 3.72 (dd, J=9.0 Hz, 6.8 Hz, 1H), 3.69-3.58 (m, 2H), 3.31 (t, J=5.5 Hz, 4H), 2.01 (s, 3H), 0.89 (t, J=5.5 Hz, 4H), 0.10 (s, 6H). $^{13}$C NMR (100 MHz, CDCl$_3$): δ171.2, 155.0 (d, J=244.3 Hz), 154.5, 138.2 (d, J=9.3 Hz), 131.5, 119.9, 114.0 (d, J=3.4 Hz), 107.6 (d, J=27.1 Hz), 71.9, 50.9, 47.7, 41.9, 23.0, 14.3, −2.9.

Preparation of Bis(bromomethyl)dimethylsilane (2) (as per scheme 2)

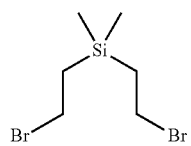

HBr gas is bubbled to a solution of dimethyl divinylsilane 1 (10.0 g, 89.28 mmols), and dibenzoylperoxide (DBP, 100 mg), in heptane (100 mL) at 0° C. for 30 min. The Reaction mixture (RM) is allowed to stir at room temperature (25° C.) for 18 h, water (200 mL) is added to the reaction mixture and the organic layer is separated. The heptane layer is washed with 2N NaOH (2 100 mL), dried and concentrated to obtain the product 2 as a colourless liquid (24.5 g) in 100% yield.

$^1$H NMR (200 MHz, CDCl3): δ 3.58-3.49 (m, 4H), 1.45-1.40 (m, 4H), 0.09 (s, 6H).

Preparation of 1-benzyl-4,4-dimethyl-1,4-azasilinane (3)

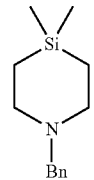

Benzylamine (20 mL, 182 mmol) and Et$_3$N (15.2 mL, 109 mmol) are added to a solution of bis-(bromomethyl) dimethylsilane 2 (10 g, 36.5 mmol) in chloroform (100 mL). The mixture is then refluxed for 16 h. 5% sodiumhydroxide solution (150 mL) is then added and the aqueous layer is extracted with dichloromethane (DCM, 2×100 mL). It is then washed with brine (200 mL), dried and concentrated. The product is purified by column chromatography on silica gel using hexane-EtOAc mixtures to obtain the product 3 as a light yellow liquid (4.3 g) in 54% yield.

$^1$H NMR (200 MHz, CDCl3): δ 7.23-7.35 (m, 5H), 3.66 (s, 2H), 2.68 (t, J=6.3 Hz, 4H), 0.75 (t, J=6.3 Hz, 4H), 0.04 (s, 6H).

Preparation of 4,4-dimethyl-1,4-azasilinane hydrochloride (4)

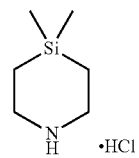

To a solution of 4,4-dimethyl-1,4-azasilinane 3 (2.3 g, 10.5 mmol) in EtOH (20 mL), 6N hydrochloricacid (1.75 mL, 10.5 mmol) is added and the solvent is removed under reduced pressure. The reaction mixture is co-evaporated with EtOH (2×10 mL) and recrystallized from EtOH-diethyl ether. To a slurry of Pd/C (50 mg) in EtOH (15 mL) an ethanolic solution of above prepared HCl salt is added drop wise and stirred at 25° C. under hydrogen atmosphere for 20 h. The reaction mixture is filtered through celite and washed with 2×20 mL of MeOH. The filtrate is then concentrated under reduced pressure to give viscous oil which was triturated with diethyl ether to obtain the product 4 as a white solid (950 mg) in 70% yield.

Preparation of 1-(2-fluoro-4-nitrophenyl)-4,4-dimethyl-1,4-azasilinane (9)

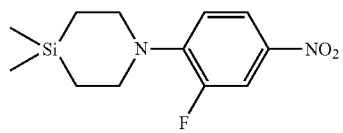 [SMILES: C[Si]1(C)CCN(c2ccc([N+](=O)[O-])cc2F)CC1]

To a solution of 4,4-dimethyl-1,4-azasilinane hydrochloride 4 (500 mg, 3.85 mmol) in EtOAc (15 mL), triethylamine (1.3 mL, 9.63 mmol) is added and stirred at 25° C. for 10 min. The reaction mixture is cooled to 0° C. and 3,4-difluoronitrobenzene (612 mg, 3.85 mmol) is added drop wise and allowed to stir at 25° C. for 6 h. Water is then added and the organic layer is separated. The aqueous layer is extracted with EtOAc (2×10 mL) and the solvent is removed under reduced pressure. The product is purified by column chromatography using hexane-EtOAc mixtures and a crystalline yellow solid 9 (721 mg) is obtained in 70% yield.

$^1$H NMR (200 MHz, CDCl$_3$): δ 7.93-7.84 (m, 2H), 6.86 (t, J=4 Hz, 1H), 3.70-3.67 (m, 4H), 0.91-0.85 (m, 4H), 0.12 (s, 6H). $^{13}$C NMR (50 MHz, CDCl$_3$): δ 151.1 (d, J=246.71 Hz), 144.4 (d, J=7.13 Hz), 137.8 (d, J=8.59 Hz), 121.4, 115.9 (d, J=4.61 Hz), 113.2 (J=27.78 Hz), 49.4, 13.8, −2.8. IR (CHCl$_3$): ν 2948, 2894, 1603, 1523, 1492, 1400, 1342, 1223, 983, 832, 742 cm$^{-1}$. M.P: 70-72° C.

Preparation of benzyl 4-(4,4-dimethyl-1,4-azasilinan-1-yl)-3-fluorophenylcarbamate (10)

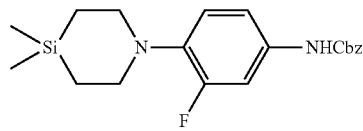 [SMILES: C[Si]1(C)CCN(c2ccc(NC(=O)OCc3ccccc3)cc2F)CC1]

To a solution of compound 9 (610 mg, 2.28 mmol) in THF (25 mL), Pd/C (30 mg) is added and hydrogenated under a pressure of 35 psi in a par hydrogenator for 8 h. The reaction mixture is filtered through celite. Celite pad is washed with THF (2×20 mL). To the filtrate, saturated NaHCO$_3$ (420 mg, 5.01 mmol) and CBzCl (427 mg, 2.5 mmol) are added at 0° C. and stirred at 25° C. for 5 h. 10 mL water is added to reaction mixture and the aqueous layer is extracted with EtOAc (2×20 mL). The crude mixture is then subjected to column chromatography on silica gel using hexane-EtOAc mixtures to afford the product as a viscous liquid 10 (690 mg) in 82% yield.

$^1$H NMR (200 MHz, CDCl$_3$): δ 7.41-7.37 (m, 5H), 6.94-6.93 (m, 2H), 6.68 (s, 1H), 5.21 (s, 1H), 3.3 (t, J=6.38 Hz, 4H), 0.93 (t, J=6.08 Hz, 4H), −0.13 (s, 6H). $^{13}$C NMR (50 MHz, CDCl$_3$): 155.4 (d, 244.4 Hz), 153.6, 136.1, 135.9, 128.6, 128.5, 128.3, 120.4, 117.2 (d, 18.7 Hz), 114.7, 108.3 (20.5 Hz), 67.1, 51.4, 14.4, −3.0. IR (CHCl$_3$): ν 3317, 2953, 2803, 1706, 1594, 1521, 1271, 1221, 1058, 869, 759 cm$^{-1}$. M.P: 80-82° C.

Preparation of (S)-5-(aminomethyl)-3-(4-(4,4-dimethyl-1,4-azasilinan-1-yl)-3-fluorophenyl)oxazolidin-2-one (11) (NDS-10057)

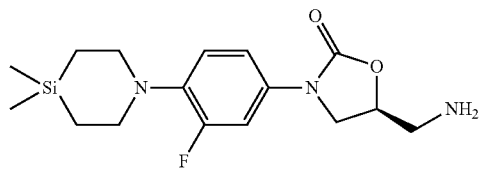 [SMILES: C[Si]1(C)CCN(c2ccc(N3C[C@H](CN)OC3=O)cc2F)CC1]

To a solution of 10 (1.20 g, 3.23 mmol) and (S)-tert-butyl 3-chloro-2-hydroxypropylcarbamate (1.35 g, 6.47 mmol) in DMF (10 mL), LiO$^t$Bu (1.03 g, 12.94 mmol) is added at 0° C. The mixture is stirred at 25° C. for 45 h. The starting material 10 is not consumed completely. Saturated NH$_4$Cl is then added; the organic phase is extracted with EtOAc (2×20 mL), washed with brine solution, dried and concentrated. The crude residue is dissolved in 20 mL of DCM-TFA mixture (8:2) and stirred at 25° C. for 3 h. RM is concentrated and dissolved in water (10 mL), the aqueous layer is washed with diethyl ether (2×50 mL), basified with saturated NaHCO$_3$ and extracted with DCM (2×50 mL). The DCM layer is dried and concentrated. The crude is purified by column chromatography on silica gel using hexane-EtOAc mixtures to obtain the product as an off-white solid (500 mg) in 45% (based on recovery of starting material) over 2 steps.

$^1$H NMR (400 MHz, CDCl$_3$): δ 7.36 (dd, J=14.2 Hz, 2.3 Hz, 1H), 7.09 (dd, J=8.8 Hz, 1.7 Hz, 1H), 6.96 (t, J=9.5 Hz, 1H), 4.72-4.59 (m, 1H), 4.00 (t, J=8.3 Hz, 1H), 3.79 (dd, J=8.7 Hz, 6.8 Hz, 1H), 3.30 (t, J=6.2 Hz, 4H), 3.03 (dq, J=13.6 Hz, 4.2 Hz, 2H), 0.90 (t, J=6.2 Hz, 4H), 0.10 (s, 6H). $^{13}$C NMR (100 MHz, CDCl$_3$): δ 155.1 (d, J=244.3 Hz), 154.7, 137.9 (d, J=9.0 Hz), 132.1 (d, J=10.3 Hz), 112.0 (d, J=4.3 Hz), 113.8 (d, J=3.2 Hz), 107.4 (d, J=26.9 Hz), 73.8, 51.0, 47.8, 45.01, 14.4, −2.9. IR (CHCl$_3$): ν 3685, 3021, 2955, 2809, 2401, 1747, 1515, 1416, 1219, 1029, 991, 870, 771, 667 cm$^{-1}$. M.P: 94-96° C. ESI-MS: 360.11 (M+Na).

Preparation of (S)—N-((3-(4-(4,4-dimethyl-1,4-azasilinan-1-yl)-3-fluorophenyl)-2-oxooxazolidin-5-yl)methy)acetamide (12) (NDS 10024)

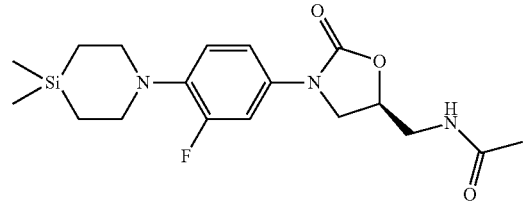 [SMILES: CC(=O)NC[C@H]1CN(c2ccc(N3CC[Si](C)(C)CC3)c(F)c2)C(=O)O1]

To solution of amine 11 (300 mg, 0.9 mmol) and DIPEA (0.3 mL, 1.78 mmol) in dry THF (4.0 mL), acetylchloride (0.08 mL, 1.07 mmol) is added at 0° C., and stirred at 25° C. for 3 h. Further, saturated NaHCO$_3$ (5.0 mL) is added to the reaction mixture and extracted with EtOAc (2×5 mL). The organic layer is washed with brine, dried and concentrated. The product is purified by column chromatography on silica gel using hexane-EtOAc mixtures to obtain the product as an off-white solid (170 mg) in 50% yield.

$^1$HNMR (400 MHz, CDCl$_3$): δ 7.33 (d, J=13.8 Hz, 1H), 7.02-6.94 (m, 2H), 6.52 (t, J=5.8 Hz, 1H), 4.77-4.73 (m, 1H), 3.99 (t, J=9.04 Hz, 1H), 3.72 (dd, J=9.0 Hz, 6.8 Hz, 1H), 3.69-3.58 (m, 2H), 3.31 (t, J=5.5 Hz, 4H), 2.01 (s, 3H), 0.89 (t, J=5.5 Hz, 4H), 0.10 (s, 6H). $^{13}$C NMR (100 MHz, CDCl$_3$): δ171.2, 155.0 (d, J=244.3 Hz), 154.5, 138.2 (d, J=9.3 Hz), 131.5, 119.9, 114.0 (d, J=3.4 Hz), 107.6 (d, J=27.1 Hz), 71.9, 50.9, 47.7, 41.9, 23.0, 14.3, −2.9. IR (CHCl$_3$): ν 2401, 1759, 1675, 1519, 1216, 759, 669 cm$^{-1}$ M.P: 123-126° C. ESI-MS: 380.10 (M+H).

N-((3-(4-(4,4-dimethyl-1,4-azasilinan-1-yl)-3-fluorophenyl)-2-oxooxazolidin-5-yl)methy)acetamide (12r):(NDS-10026)

$^1$HNMR (200 MHz, CDCl$_3$): δ 7.33 (d, J=13.8 Hz, 1H), 7.02-6.94 (m, 2H), 6.52 (t, J=5.8 Hz, 1H), 4.77-4.73 (m, 1H), 3.99 (t, J=9.04 Hz, 1H), 3.72 (dd, J=9.0 Hz, 6.8 Hz, 1H), 3.69-3.58 (m, 2H), 3.31 (t, J=5.5 Hz, 4H), 2.01 (s, 3H), 0.89 (t, J=5.5 Hz, 4H), 0.10 (s, 6H). $^{13}$C NMR (100 MHz, CDCl$_3$): δ171.2, 155.0 (d, J=244.3 Hz), 154.5, 138.2 (d, J=9.3 Hz), 131.5, 119.9, 114.0 (d, J=3.4 Hz), 107.6 (d, J=27.1 Hz), 71.9, 50.9, 47.7, 41.9, 23.0, 14.3, −2.9. IR (CHCl$_3$): ν 2401, 1759, 1675, 1519, 1216, 759, 669 cm$^{-1}$

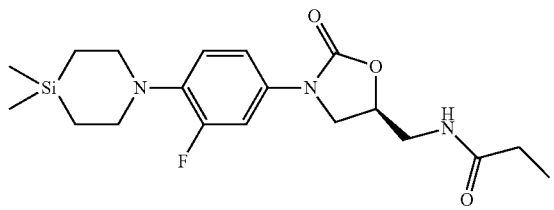 [SMILES: CCC(=O)NC[C@H]1CN(c2ccc(N3CC[Si](C)(C)CC3)c(F)c2)C(=O)O1]

Preparation of (S)—N-((3-(4-(4,4-dimethyl-1,4-aza-silinan-1-yl)-3-fluorophenyl)-2-oxooxazolidin-5-yl)ethyl)propionamide (13) (NDS 10033)

To solution of amine 11 (100 mg, 0.3 mmol) and DIPEA (0.11 mL, 0.6 mmol) in dry THF (4.0 mL), propionylchloride (0.03 mL, 0.35 mmol) is added at 0° C., and stirred at 25° C. for 3 h. Saturated NaHCO₃ (5.0 mL) is added to the reaction mixture and extracted with EtOAc (2×5 mL). The organic layer is washed with brine, dried and concentrated. The product is then purified by column chromatography on silica gel using hexane-EtOAc mixtures to obtain the product as an off-white solid (60 mg) in 54% yield.

$^1$H NMR (400 MHz, CDCl₃): δ 7.34 (dd, J=14.20 Hz, 2.07 Hz, 1H), 7.05-6.90 (m, 2H), 5.98 (t, J=6.0 Hz, 1H), 4.78-4.68 (m, 1H), 3.99 (t, J=9.21 Hz, 1H), 3.76-3.60 (m, 3H), 3.30 (t, J=6.16 Hz, 4H), 2.22 (q, J=7.62 Hz, 2H), 1.12 (t, J=7.62 Hz, 3H), 0.92-0.86 (m, 4 Hz), 0.09 (s, 6H). $^{13}$C NMR (100 MHz, CDCl₃): 175.0, 154.5, 155.0 (d, J=245.1 Hz), 138.2 (d, J=9.4 Hz), 131.5 (d, J=10.8 Hz), 119.9 (d, J=3.9 Hz), 114.0 (d, J=3.1 Hz), 107.6 (d, J=27 Hz), 72.0, 51.0, 47.7, 41.9, 29.5, 14.4, 9.8, −3.0. IR (CHCl₃): ν 3449, 2401, 1753, 1672, 1516, 1216, 759, 669 cm⁻¹.

M.P: 135-137° C. ESI-MS: 416.09 (M+Na)

Preparation of (S)-methyl((3-(4-(4,4-dimethyl-1,4-azasilinan-1-yl)-3-fluorophenyl)-2-oxooxazolidin-5-yl)methyl)carbamate (14) (NDS-10061)

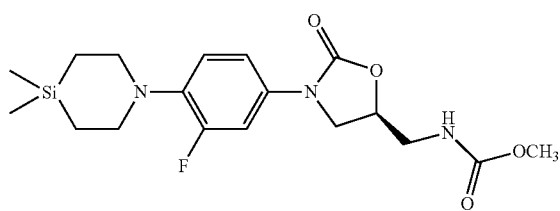 [SMILES: COC(=O)NC[C@H]1CN(c2ccc(N3CC[Si](C)(C)CC3)c(F)c2)C(=O)O1]

To a solution of amine 11 (150 mg, 0.44 mmol) in DCM (5.0 mL), Et₃N (0.18 mL, 1.34 mmol) and carbonyldiimadazole (108 mg, 0.67 mmol) are added and stirred at 25° C. for 4 h. The reaction mixture is then concentrated to one third of its volume. To this crude, MeOH (5 mL) and DCM (5 mL) are added and stirred at 25° C. for 24 h. The product is then purified by column chromatography on silica gel using hexane-EtOAc mixtures to obtain the product as an off-white solid (65 mg) in 37% yield.

$^1$H NMR (200 MHz, CDCl₃): δ 7.34 (dd, J=13.8 Hz, 1.9 Hz, 1H), 7.09-6.91 (m, 2H), 5.12 (t, J=5.8 Hz, 1H), 4.80-4.68 (m, 1H), 4.01 (t, J=9.0 Hz, 1H), 3.79-3.75 (m, 1H), 3.68 (s, 3H), 3.62-3.47 (m, 2H), 3.31 (t, J=6.0 Hz, 4H), 0.90 (t, J=6.0 Hz, 4H), 0.10 (s, 6H). $^{13}$C NMR (50 MHz, CDCl₃): δ 155.1 (d, J=245.7 Hz), 154.3, 152.4, 138.2 (d, J=9.5 Hz), 131.6 (d, J=10.4 Hz), 119.9 (d, J=4.2 Hz), 114.0 (d, J=2.9 Hz), 107.6 (d, J=26.8 Hz), 71.7, 52.6, 51.0, 47.6, 43.72, 14.4, −2.9. IR (CHCl₃): ν 3684, 3450, 2401, 1755, 1725, 1515, 1216, 755, 669 cm⁻¹.

M.P: 152-154° C. ESI-MS: 418.10 (M+Na).

Preparation of (S)—O-methyl((3-(4-(4,4-dimethyl-1,4-azasilinan-1-yl)-3-fluorophenyl)-2-oxooxazolidin-5-yl)methyl)carbamothioate (15) (NDS-10062)

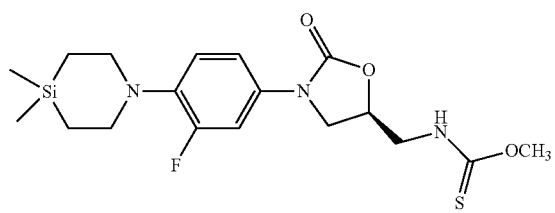 [SMILES: COC(=S)NC[C@H]1CN(c2ccc(N3CC[Si](C)(C)CC3)c(F)c2)C(=O)O1]

To a solution of amine 11 (150 mg, 0.45 mmol) in DCM (5 mL), saturated NaHCO₃ (2 mL) is added and cooled to 0° C. Further, to this reaction mixture, thiophosgene (0.04 mL, 0.58 mmol) is added and stirred at RT for 3 h. The DCM layer is separated and aqueous layer is extracted with DCM (2×5 mL). Further, the combined organic layers were washed with brine, dried and concentrated. The crude obtained is then dissolved in MeOH (5 mL) and refluxed for overnight. RM is concentrated and dissolved in EtOAc, washed with saturated NaHCO₃, dried and concentrated. The crude is then purified by column chromatography on silica gel using hexane-EtOAc mixtures to obtain the product as an off-white solid (75 mg) in 40% yield.

$^1$H NMR (400 MHz, CDCl₃): δ 7.34 (dd, J=13.9 Hz, 1.9 Hz, 1H), 7.07-6.91 (m, 2H), 6.73 (t, J=6.2 Hz, 1H), 4.96-4.83 (m, 1H), 4.15-4.04 (m, 2H), 4.00 (s, 3H), 3.95-3.76 (m, 2H), 3.32 (t, J=6.2 Hz, 4H), 0.90 (t, J=6.2 Hz, 4H), 0.10 (s, 6H).

$^{13}$C NMR (100 MHz, CDCl₃): δ 192.8, 154.4, 155.0 (d, J=244.6 Hz), 138.2 (d, J=9.4 Hz), 131.5 (d, J=10.8 Hz), 119.9 (d, J=4.4 Hz), 114.1 (d, J=3.2 Hz), 107.6 (d, J=26.8 Hz), 71.3, 57.7, 51.0, 47.6, 14.4, −2.9. IR (CHCl₃): ν 3685, 3400, 2953, 2401, 1755, 1515, 1216, 755, 669 cm⁻¹. M.P: 123-126° C. ESI-MS: 434.14 (M+Na).

Preparation of (R)-3-(4-(4,4-dimethyl-1,4-azasilinan-1-yl)-3-fluorophenyl)-5-(hydroxymethyl)oxazolidin-2-one (17) (NDS-10059)

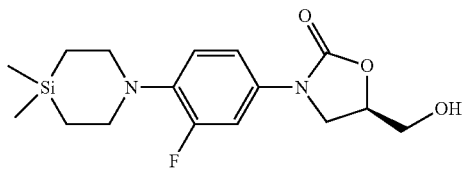 [SMILES: C[Si]1(C)CCN(c2ccc(N3C[C@H](CO)OC3=O)cc2F)CC1]

To the Cbz compound 10 (800 mg, 2.15 mmol) in dry THF (5 mL) at −78° C., n-BuLi 2.0 M (4.0 mL, 3.87 mmol) is added and stirred for 30 min. Further, glycidylbutyrate 16 (0.6 mL, 3.87 mmol) is added drop wise at −78° C., and allowed to stir at 25° C. for overnight. RM is then quenched with saturated NH₄Cl (5 mL), extracted with EtOAc (2×10 mL), and the organic layer is washed with brine (5 mL), dried and concentrated. The product is purified by column chromatography on silica gel using hexane-EtOAc mixtures to obtain the product as an off-white solid (420 mg) 58% yield.

$^1$H NMR (200 MHz, CDCl$_3$): δ 7.36 (dd, J=14.4 Hz, 2.4 Hz, 1H), 7.09 (dd, J=9.4 Hz, 2.3 Hz, 1H), 7.01-6.92 (m, 1H), 4.80-4.68 (m, 1H), 4.18-3.87 (m, 4H), 3.32 (t, J=6.2 Hz, 4H), 2.18 (bs, 1H), 0.90 (t, J=6.2 Hz, 4H), 0.11 (s, 6H). $^{13}$C NMR (50 MHz, CDCl$_3$): δ 155.1 (d, J=244.9 Hz), 154.9, 138.1 (d, J=8.6 Hz), 131.9 (d, J=10.1 Hz), 112.0 (d, J=4.1 Hz), 114.0 (d, J=3.4 Hz), 107.5 (d, J=26.7 Hz), 73.0, 62.7, 51.0, 50.98, 14.4, −2.9. IR (CHCl$_3$): ν 3407, 2953, 2922, 1738, 1517, 1418, 1384, 1249, 1231, 1199, 990, 870, 757 cm$^{-1}$. M.P: 126-129° C.

ESI-MS: 361.08 (M+Na).

Preparation of (R)-(3-(4-(4,4-dimethyl-1,4-azasilinan-1-yl)-3-fluorophenyl)-2-oxooxazolidin-5-yl)methyl methanesulfonate (18)

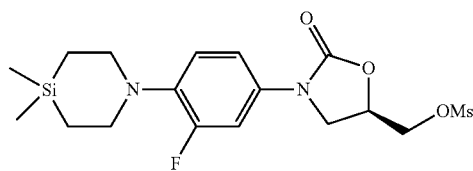 [SMILES: C[Si]1(C)CCN(c2ccc(N3C[C@H](COS(C)(=O)=O)OC3=O)cc2F)CC1]

To a solution of alcohol 17 (200 mg, 0.59 mmol) and Et$_3$N (0.16 mL, 1.18 mmol) in dry DCM (5 mL), MsCl (0.068, 0.88 mmol) is added at 0° C. and stirred at 25° C. for 2 h. Saturated NaHCO$_3$ (5 mL) is added, layers are separated, aqueous layer is extracted with DCM (2×5 mL), dried and concentrated. The crude (250 mg) is directly carried to next step.

Preparation of (R)-5-(azidomethyl)-3-(4-(4,4-dimethyl-1,4-azasilinan-1-yl)-3-fluorophenyl)oxazolidin-2-one (19)

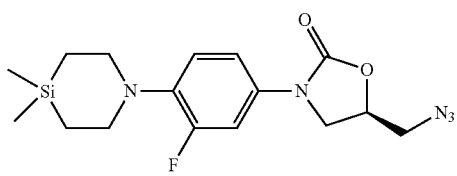 [SMILES: C[Si]1(C)CCN(c2ccc(N3C[C@H](CN=[N+]=[N-])OC3=O)cc2F)CC1]

To the Mesyl compound 18 (250 mg, 0.59 mmol) in DMF, NaN$_3$ (78 mg, 1.20 mmol) is added and stirred at 60° C. for 2 h. Water (5 mL) is then added and extracted with DCM (2×5 mL), dried and concentrated. The crude (220 mg) is used for further steps without purification.

Preparation of (R)-5-((1H-1,2,3-triazol-1-yl)methyl)-3-(4-(4,4-dimethyl-1,4-azasilinan-1-yl)-3-fluorophenyl)oxazolidin-2-one (21) (NDS-10060)

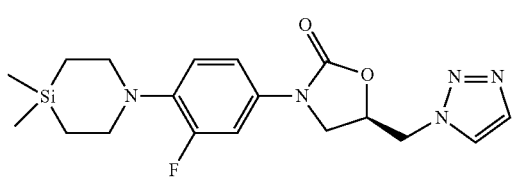 [SMILES: C[Si]1(C)CCN(c2ccc(N3C[C@H](Cn4ccnn4)OC3=O)cc2F)CC1]

A solution of azide 19 (0.60 mmol) and bicyclodiene 20 (0.31 mL, 3.03 mmol) in dioxane (4.0 mL) is refluxed for 5 h. Water (5 mL) is added and extracted with DCM (2×5 mL), dried and concentrated. The product is further purified by column chromatography on silica using hexane-EtOAc mixtures to obtain the product as a brown solid (60 mg) in 26% over 3 steps.

$^1$H NMR (200 MHz, CDCl$_3$): δ 7.76 (dd, J=8.8 Hz, 0.9 Hz, 2H), 7.23-7.15 (m, 1H), 6.90 (dd, J=4.6 Hz, 1.6 Hz, 2H), 5.08-4.96 (m, 1H), 4.78-4.75 (m, 2H), 4.16-4.06 (m, 1H), 3.85 (dd, J=9.4 Hz, 6.2 Hz, 2H), 3.29 (t, J=6.2 Hz, 4H), 0.87 (t, J=6.2 Hz, 4H), 0.08 (s, 6H). $^{13}$C NMR (50 MHz, CDCl$_3$): δ 154.9 (d, J=245.5 Hz), 153.6, 134.5, 138.5 (d, J=9.0 Hz), 130.7 (d, J=10.1 Hz), 125.1, 119.9, 119.9 (d, J=4.06 Hz), 114.5 (d, J=3.3 Hz), 108.0 (d, J=26.7 Hz), 70.4, 52.0, 50.8, 50.8, 47.5, 14.3, −2.9. IR (neat): 2401, 1760, 1515, 1216, 770, 669 cm$^{-1}$.

M.P. 165-168° C. ESI-MS: 412.04 (M+Na).

The following Compounds were prepared by using above schemes 1-4 and the procedures described above.

22 (NDS-10054)

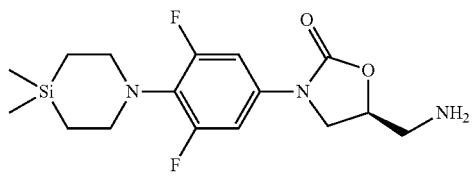

28 (NDS-10058)

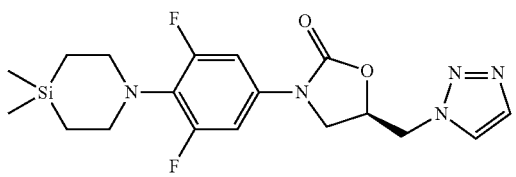

23 (NDS-10028)

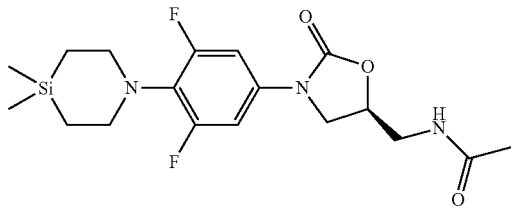

29 (NDS-10070)

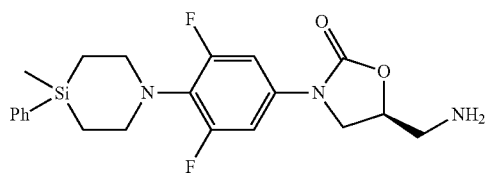

24 (NDS-10056)

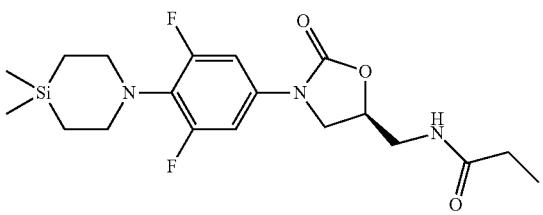

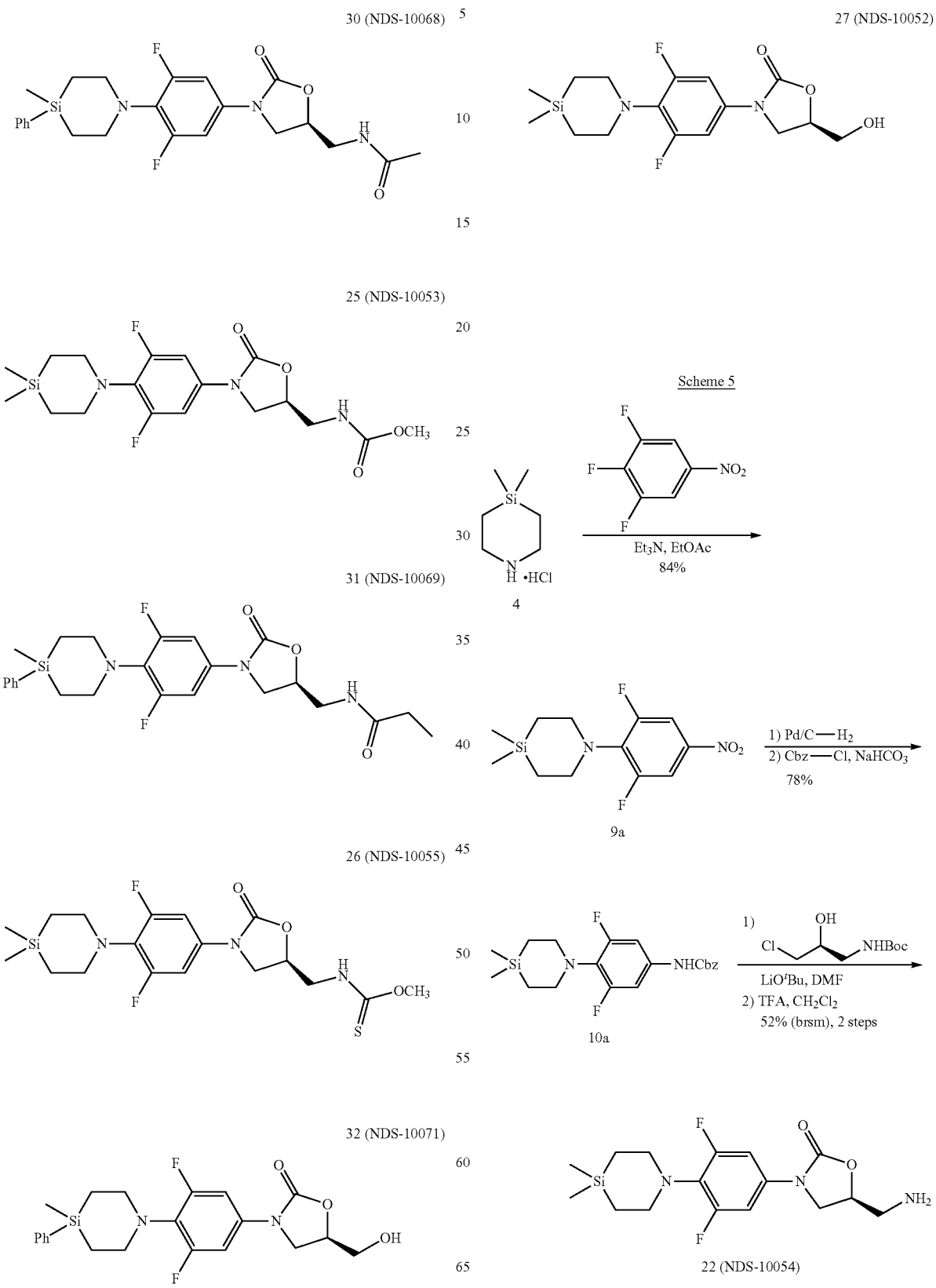

Scheme 6

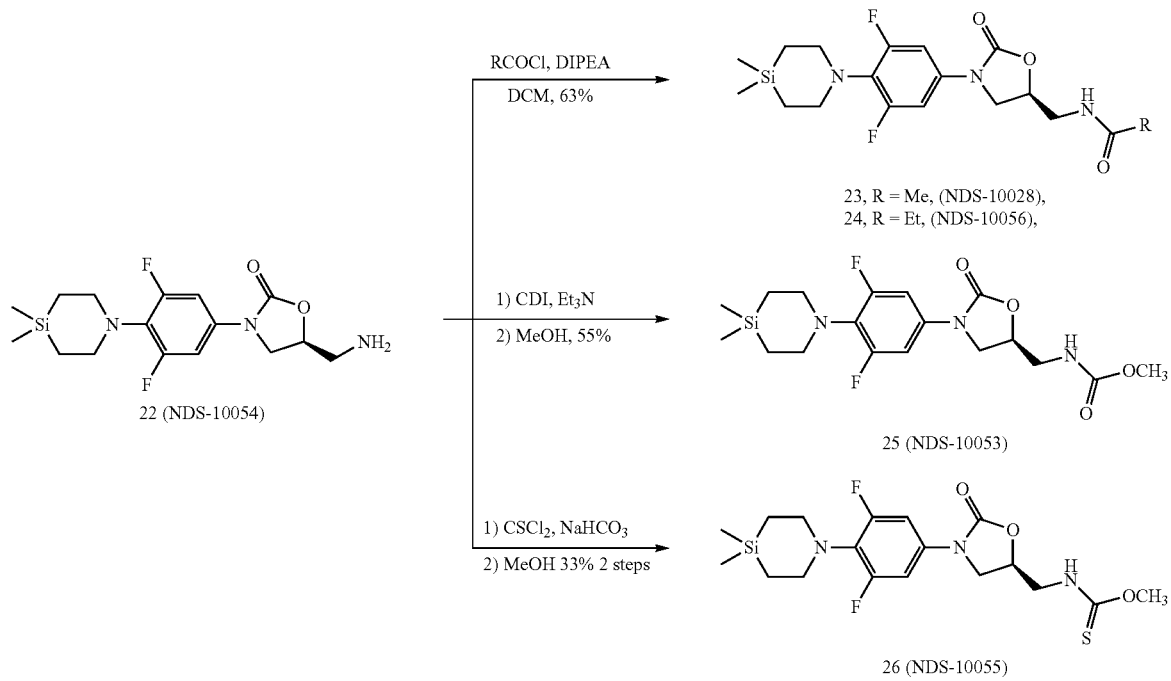

Preparation of 1-(2,6-difluoro-4-nitrophenyl)-4,4-dimethyl-1,4-azasilinane (9a)

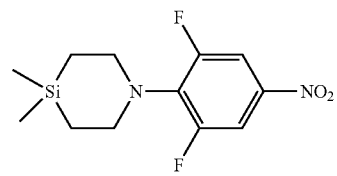 [SMILES: C[Si]1(C)CCN(c2c(F)cc([N+](=O)[O-])cc2F)CC1]

To a solution of 4,4-dimethyl-1,4-azasilinane hydrochloride 4 (950 mg, 7.35 mmol) in EtOAc (15 mL), triethylamine (2.5 mL, 18.37 mmol) is added and stirred at 25° C. for 10 min. The reaction mixture is cooled to 0° C. and 1,2,3-trifluoro-5-nitrobenzene (1.29 g, 7.35 mmol) is added drop wise and allowed to stir at 25° C. for 6 h. Water is then added and the organic layer is separated. The aqueous layer is extracted with EtOAc (2×10 mL) and the solvent is removed under reduced pressure. The product obtained is purified by column chromatography using hexane-EtOAc mixtures to give the product as a crystalline yellow solid 9a (1.32 g) in 63% yield.

$^1$H NMR (400 MHz, CDCl$_3$): δ 7.77-7.69 (m, 2H), 3.51 (t, J=6.28 Hz, 4H), 0.90 (t, J=6.28 Hz, 4H), 0.12 (s, 6H). $^{13}$C NMR (50 MHz, CDCl$_3$): δ 155.05 (dd, J=248.5 Hz, 8.40 Hz), 108.9 (m), 138.96 (d, J=10.98 Hz), 136.73 (t, J=12.44 Hz), 51.04 (t, J=4.02 Hz), 15.15, −3.07. IR: 1606, 1515, 1335, 1216, 1110, 758 cm$^{-1}$.

Preparation of benzyl(4-(4,4-dimethyl-1,4-azasilinan-1-yl)-3,5-difluorophenyl)carbamate (10a)

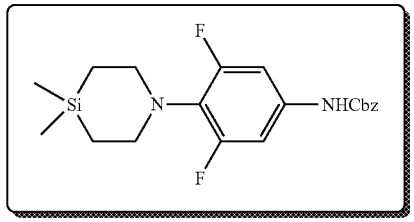

To a solution of 9a (1.32 g, 4.61 mmol) in THF, Pd/C is added for hydrogenation under a pressure of 35 psi in a par hydrogenator. The reaction mixture is filtered through celite. To the filtrate, saturated NaHCO$_3$ (1.16 g, 13.84 mmol), CBzCl (1.17 g, 6.93 mmol) are added and stirred at 25° C. for 5 h. The solvent is removed, 10 mL water is then added and the aqueous layer is extracted with EtOAc. The crude mixture is then subjected to column chromatography on silica gel using hexane-DCM mixtures to afford the product 10a as a viscous liquid (1.25 g) in 69% yield.

$^1$H NMR (200 MHz, CDCl$_3$): δ 7.40-7.34 (m, 5H), 6.97-6.83 (m, 2H), 6.58 (bs, 1H), 5.17 (s, 2H), 3.26 (t, J=6.19 Hz, 4H), 0.85 (t, J=6.19 Hz, 4H), 0.09 (s, 6H). $^{13}$C NMR (50 MHz, CDCl$_3$): δ 159.04 (dd, J=246.9 Hz, 9.4 Hz), 153.24, 135.83, 133.56 (t, J=13.5 Hz), 128.66, 128.47, 128.35, 126.36 (t, J=14.6 Hz), 102.79 (d, J=29.5 Hz), 67.24, 51.88, 15.54, −2.94.

Preparation of (S)-5-(aminomethyl)-3-(4-(4,4-dimethyl-1,4-azasilinan-1-yl)-3,5-difluorophenyl)oxazolidin-2-one (22) (NDS-10054)

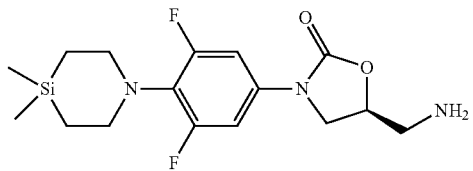 [SMILES: C[Si]1(C)CCN(c2c(F)cc(N3C[C@H](CN)OC3=O)cc2F)CC1]

To a solution of 10a (1.10 g, 2.81 mmol) and (S)-tert-butyl 3-chloro-2-hydroxypropylcarbamate (1.06 g, 5.06 mmol) in DMF (10 mL), LiO$^t$Bu (675 mg, 8.43 mmol) is added at 0° C. The mixture is stirred at 25° C. for 45 h. The starting material 10a is not consumed completely. Saturated NH$_4$Cl is then added and the organic phase is extracted with EtOAc (2×20 mL), washed with brine solution, dried and concentrated. The crude residue is dissolved in 20 mL of DCM-TFA mixture (8:2) and stirred at 25° C. for 3 h. RM is concentrated and dissolved in water (10 mL), the aqueous layer is washed with diethyl ether (2×50 mL), basified with saturated NaHCO$_3$ and extracted with DCM (2×50 mL), and the DCM layer is dried and concentrated. The crude is purified by column chromatography on silica gel using hexane-EtOAc mixtures to obtain the product as an off-white solid (650 mg) in 65% (based on recovery of starting material) over 2 steps.

$^1$H NMR (400 MHz, CDCl$_3$): δ 6.93-6.85 (m, 2H), 4.90-4.87 (m, 1H), 3.92 (t, J=9.0 Hz, 1H), 3.67 (dd, J=9.06 Hz, 6.30 Hz, 1H), 3.17 (dd, J=13.6 Hz, 4.0 Hz, 1H), 3.12 (t, J=6.15 Hz, 4H), 3.05 (dd, J=13.7 Hz, 7.42 Hz, 1H), 0.69 (t, J=6.15 Hz, 4H), 0.07 (s, 6H). $^{13}$C NMR (100 MHz, CDCl$_3$): δ 158.1 (dd, J=244.6 Hz, 9.9 Hz), 153.3, 134.1, 125.3, 102.3 (m), 69.6, 51.4, 47.0, 41.6, 15.0, −3.1. IR (CHCl$_3$): ν 3685, 3021, 2955, 2809, 2401, 1747, 1515, 1416, 1219, 1029, 991, 870, 771, 667 cm$^{-1}$. M.P: 180-182° C. ESI-MS: 378.10 (M+Na).

Preparation of (S)—N-((3-(4-(4,4-dimethyl-1,4-azasilinan-1-yl)-3,5-difluorophenyl)-2-oxooxazolidin-5-yl)methyl)acetamide (23) (NDS-10028)

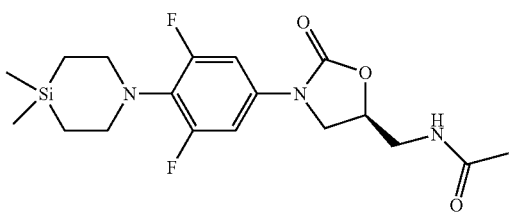 [SMILES: CC(=O)NC[C@H]1CN(c2cc(F)c(N3CC[Si](C)(C)CC3)c(F)c2)C(=O)O1]

To solution of amine 22 (200 mg, 0.56 mmol) and DIPEA (0.2 mL, 1.12 mmol) in dry THF (4.0 mL), acetylchloride (0.06 mL, 0.84 mmol) is added at 0° C., and stirred at 25° C. for 3 h. Saturated NaHCO$_3$ (5.0 mL) is then added to the reaction mixture and extracted with EtOAc (2×5 mL). Further, the organic layer is washed with brine, dried and concentrated. The product is purified by column chromatography on silica gel using hexane-EtOAc mixtures to obtain the product as an off-white solid (150 mg) in 67% yield.

$^1$H NMR (500 MHz, CDCl$_3$): δ 7.08-7.01 (m, 2H), 6.00 (t, J=5.42 Hz, 1H), 4.79-4.73 (m, 1H), 3.98 (t, J=8.68 Hz, 1H), 3.73-3.67 (m, 2H), 3.63-3.56 (m, 1H), 3.29 (t, J=6.01 Hz, 4H), 2.02 (s, 3H), 087 (t, J=6.01 Hz, 4H), 0.10 (s, 6H). $^{13}$C NMR (125 MHz, CDCl$_3$): δ 171.3, 158.0 (dd, J=245.9 Hz, 9.3 Hz), 154.2, 133.0 (t, J=14.1 Hz), 127.1 (t, J=14.4 Hz), 102.4 (m), 72.0, 51.7, 47.5, 41.9, 23.0, 15.5, −3.0. IR (CHCl$_3$): ν 2400, 1757, 1675, 1216, 759, 669 cm$^{-1}$.
M.P: 136-139° C. ESI-MS: 420.09 (M+Na).

Preparation of (S)—N-((3-(4-(4,4-dimethyl-1,4-azasilinan-1-yl)-3,5-difluorophenyl)-2-oxooxazolidin-5-yl)methyl)propionamide (24): (NDS-10056)

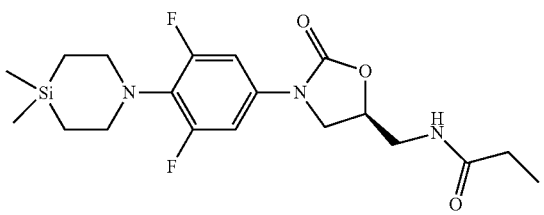 [SMILES: CCC(=O)NC[C@H]1CN(c2cc(F)c(N3CC[Si](C)(C)CC3)c(F)c2)C(=O)O1]

To solution of amine 22 (80 mg, 0.22 mmol) and diisopropylethylamine (0.07 mL, 0.45 mmol) in dry THF (4.0 mL), propionylchloride (0.02 mL, 0.22 mmol) is added at 0° C., and stirred at 25° C. for 3 h. Further, saturated NaHCO$_3$ (5.0 mL) is added to the reaction mixture and extracted with EtOAc (2×5 mL), the organic layer is washed with brine, dried and concentrated. The product is purified by column chromatography on silica gel using hexane-EtOAc mixtures to obtain the product as an off-white solid (60 mg) in 63% yield.

$^1$H NMR (400 MHz, CDCl$_3$): δ 7.12-6.96 (m, 2H), 6.01 (t, J=5.8 Hz, 1H), 4.82-4.70 (m, 1H), 3.75-3.60 (m, 3H), 3.29 (t, J=6.0 Hz, 4H), 2.24 (q, J=7.65 Hz, 2H), 1.13 (t, J=7.65 Hz, 3H), 0.86 (t, J=6.02 Hz, 4H), 0.10 (s, 6H). $^{13}$C NMR (100 MHz, CDCl$_3$): δ 175.1, 158.7 (d, J=236.8 Hz), 154.2, 133.1, 127.0, 102.3 (d, J=30.9 Hz), 72.0, 51.8, 47.5, 41.8, 29.5, 15.4, 9.8, −3.0. IR (CHCl$_3$): ν 2925, 2401, 1753, 1671, 1510, 1216, 759, 669 cm$^{-1}$.
M.P: 144-146° C. ESI-MS: 434.15 (M+Na).

Preparation of (S)-methyl(3-(4-(4,4-dimethyl-1,4-azasilinan-1-yl)-3,5-difluorophenyl)-2-oxooxazolidin-5-yl)methylcarbamate (25): (NDS-10053)

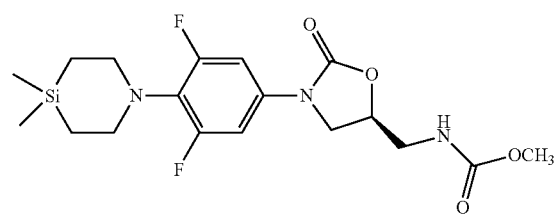 [SMILES: COC(=O)NC[C@H]1CN(c2cc(F)c(N3CC[Si](C)(C)CC3)c(F)c2)C(=O)O1]

To a solution of amine 22 (100 mg, 0.28 mmol) in DCM (5.0 mL), Et$_3$N (0.12 mL, 0.84 mmol) and carbonyldiimidazole (68 mg, 0.42 mmol) are added and stirred at 25° C. for 4 h, the reaction mixture is then concentrated to one third of its volume. To this crude, MeOH (5 mL) and DCM (5 mL) are added and stirred at 25° C. for 24 h. The product is purified by column chromatography on silica gel using hexane-EtOAc mixtures to obtain the product as an off-white solid (62 mg) in 55% yield.

$^1$H NMR (500 MHz, CDCl$_3$): 7.06-7.00 (m, 2H), 5.29 (bs, 1H), 4.76-4.71 (m, 1H), 3.96 (t, J=8.85 Hz, 1H), 3.70 (t, J=7.32 Hz, 1H), 3.67 (s, 3H), 3.61-3.49 (m, 2H), 3.27 (t, J=6.10 Hz, 4H), 0.85 (t, J=6.10 Hz), 0.09 (s, 6H).
$^{13}$C NMR (125 MHz, CDCl$_3$): δ 158.7 (dd, J=246.2 Hz, 9.3 Hz), 157.5, 153.9, 133.2 (t, J=13.2 Hz), 127.0 (t, J=14.4 Hz), 102.34 (m), 71.8, 52.9, 51.7, 47.3, 43.6, 15.5, −3.0. IR (CHCl₃): v 2924, 1746, 1512, 1250, 1124 cm⁻¹. M.P: 117-119° C. ESI-MS: 436.09 (M+Na).

Preparation of (S)—O-methyl(3-(4-(4,4-dimethyl-1,4-azasilinan-1-yl)-3,5-difluorophenyl)-2-oxooxazolidin-5-yl)methylcarbamothioate (26) (NDS-10055)

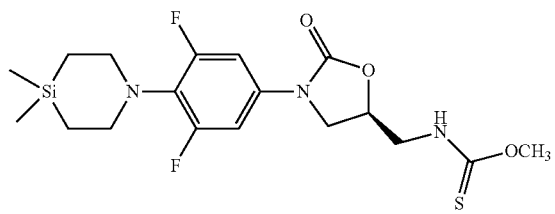 [SMILES: COC(=S)NC[C@H]1CN(c2cc(F)c(N3CC[Si](C)(C)CC3)c(F)c2)C(=O)O1]

To a solution of amine 22 (200 mg, 0.56 mmol) in DCM (5 mL), saturated NaHCO₃ (2 mL) is added, and cooled to 0° C. Further, thiophosgene (0.05 mL, 0.73 mmol) is added and stirred at 25° C. for 3 h, the DCM layer is separated and aqueous layer is extracted with DCM (2×5 mL). The combined organic layers are washed with brine, dried and concentrated. The crude is dissolved in MeOH (5 mL) and refluxed for overnight. RM is concentrated and dissolved in EtOAc, washed with saturated NaHCO₃, dried and concentrated. The crude is purified by column chromatography on silica gel using hexane-EtOAc mixtures to obtain the product as an off-white solid (80 mg) in 33% yield.

¹H NMR (500 MHz, CDCl₃): δ 7.12-6.97 (m, 2H), 6.76 (t, J=6.07 Hz, 1H), 4.97-4.85 (m, 1H), 4.13-3.93 (m, 6H), 3.79 (dd, J=9.04 Hz, 6.98 Hz, 1H), 3.29 (t, J=6.26 Hz, 4H), 0.87 (t, J=6.26 Hz, 4H), 0.10 (s, 6H). ¹³C NMR (125 MHz, CDCl₃): δ 192.9, 158.7 (dd, J=245.9, 10.3), 154.0, 133.0 (t, J=12.8 Hz), 127.1 (t, J=14.6 Hz), 102.4 (m), 71.3, 57.8, 51.8, 47.4, 47.3, 15.5, −3.0. IR (CHCl₃): v 3400, 3292, 2831, 2401, 1759, 1635, 1511, 1449, 1386, 1216, 868, 751, 669 cm⁻¹. M.P: 141-143° C. ESI-MS: 468.08 (M+K).

Scheme 7

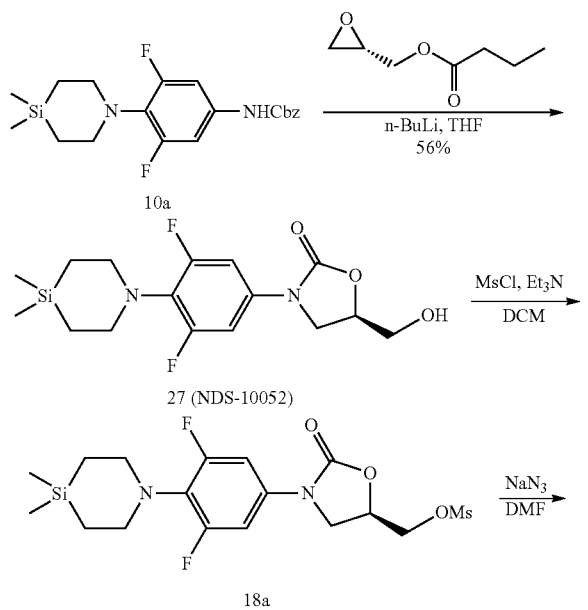

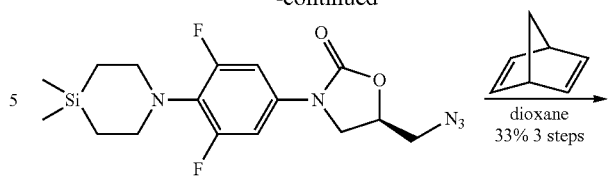

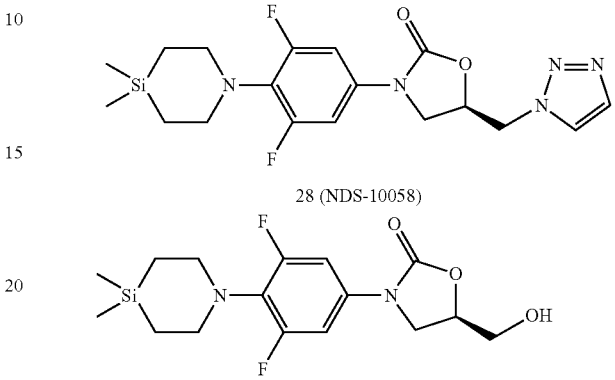

Preparation of (R)-3-(4-(4,4-dimethyl-1,4-azasilinan-1-yl)-3,5-difluorophenyl)-5-(hydroxymethyl)oxazolidin-2-one (27): (NDS-10052)

To the Cbz compound 10a (100 mg, 0.25 mmol) in dry THF (5 mL) at −78° C., n-BuLi 2.0 M (0.15 mL, 0.28 mmol) is added, stirred for 30 min and then glycidylbutyrate 16 (0.04 mL, 0.0.28 mmol) is added drop wise at −78° C., and allowed to stir at 25° C. for overnight. RM is quenched with saturated NH₄Cl (5 mL) and extracted with EtOAc (2×10 mL). The organic layer is washed with brine (5 mL), dried and concentrated. The product is purified by column chromatography on silica gel using hexane-EtOAc mixtures to obtain the product as an off-white solid (75 mg) 82% yield.

¹H NMR (400 MHz, CDCl₃): δ7.11-7.03 (m, 2H), 4.75-4.70 (m, 1H), 3.91-3.87 (m, 3H), 3.74 (t, J=12 Hz, 1H), 3.28 (t, J=6.19 Hz, 4H), 0.09 (s, 6H).

¹³C NMR (100 MHz, CDCl₃): δ 158.7 (dd, J=245.6, 9.7), 154.3, 133.3 (t, J=13.6 Hz), 126.9 (t, J=14.7 Hz), 102.3 (m), 72.7, 62.7, 51.8, 46.2, 15.5, −3.0.

ESI-MS: IR (CHCl₃): v 3401, 2401, 1754, 1511, 1252, 1260 cm⁻¹. M.P: 126-128° C. ESI-MS: 379.02 (M+Na).

Preparation of (R)-(3-(4-(4,4-dimethyl-1,4-azasilinan-1-yl)-3,5-difluorophenyl)-2-oxooxazolidin-5-yl) methyl methanesulfonate (18a)

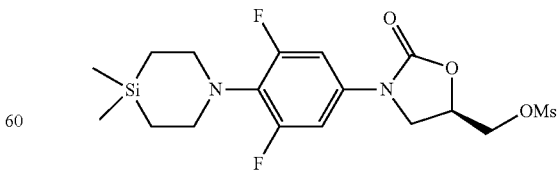

To a solution of alcohol 27 (250 mg, 0.70 mmol) and Et₃N (0.20 mL, 1.40 mmol) in dry DCM (5 mL), MsCl (0.08, 1.05 mmol) is added at 0° C. and stirred at 25° C. for 2 h. Further, saturated NaHCO₃ (5 mL) is added, layers are separated, aqueous layer is extracted with DCM (2×5 mL), dried and concentrated. The crude (320 mg) is directly carried to next step.

Preparation (R)-5-(azidomethyl)-3-(4-(4,4-dimethyl-1,4-azasilinan-1-yl)-3,5-difluorophenyl)oxazolidin-2-one (19a)

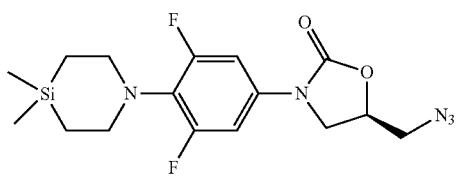 [SMILES: C[Si]1(C)CCN(c2c(F)cc(N3C[C@H](CN=[N+]=[N-])OC3=O)cc2F)CC1]

To the Mesyl compound 18a (320 mg, 0.74 mmol) in DMF, NaN₃ (63 mg, 0.97 mmol) is added and stirred at 60° C. for 2 h. Water (5 mL) is added and extracted with DCM (2×5 mL), dried and concentrated. The crude (300 mg) is used for further steps without purification.

Preparation of (R)-5-((1H-1,2,3-triazol-1-yl)methyl)-3-(4-(4,4-dimethyl-1,4-azasilinan-1-yl)-3,5-difluorophenyl)oxazolidin-2-one (28) (NDS-10058)

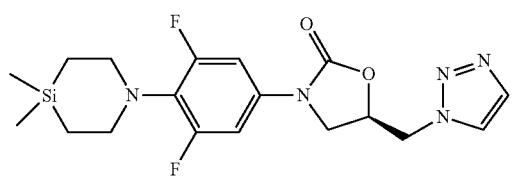 [SMILES: C[Si]1(C)CCN(c2c(F)cc(N3C[C@H](Cn4ccnn4)OC3=O)cc2F)CC1]

A solution of azide 19a (300 mg, 0.78 mmol) and bicyclodiene 20 (0.40 mL, 3.9 mmol) in dioxane (4.0 mL) is refluxed for 5 h. Water (5 mL) is added and it is extracted with DCM (2×5 mL), dried and concentrated. The product is purified by column chromatography on silica using hexane-EtOAc mixtures to obtain the product as a brown solid (140 mg) in 40% over 3 steps.

$^1$H NMR (500 MHz, CDCl₃): δ 7.76 (d, J=4.4 Hz, 2H), 7.01-6.85 (m, 2H), 5.11-4.99 (m, 1H), 4.98 (d, J=4.1 Hz, 2H), 4.09 (t, J=9.3 Hz, 1H), 3.86 (dd, J=9.1 Hz, 6.3 Hz, 1H), 3.28 (t, J=5.8 Hz, 4H), 0.85 (t, J=5.8 Hz, 4H), 0.09 (s, 6H).
$^{13}$C NMR (125 MHz, CDCl₃): δ 158.7 (dd, J=246.1, 9.4 Hz), 153.1, 134.5, 132.4 (t, J=12.8 Hz), 125.1, 127.4 (t, J=14.1 Hz), 102.7 (m), 70.4, 52.0, 51.7, 47.2, 15.4, −3.0. IR (CHCl₃): ν 2401, 1767, 1635, 1511, 1216, 757, 669 cm⁻¹. M.P: 149-151° C. ESI-MS: 430.09 (M+Na).

Scheme 8

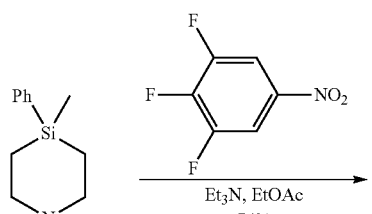

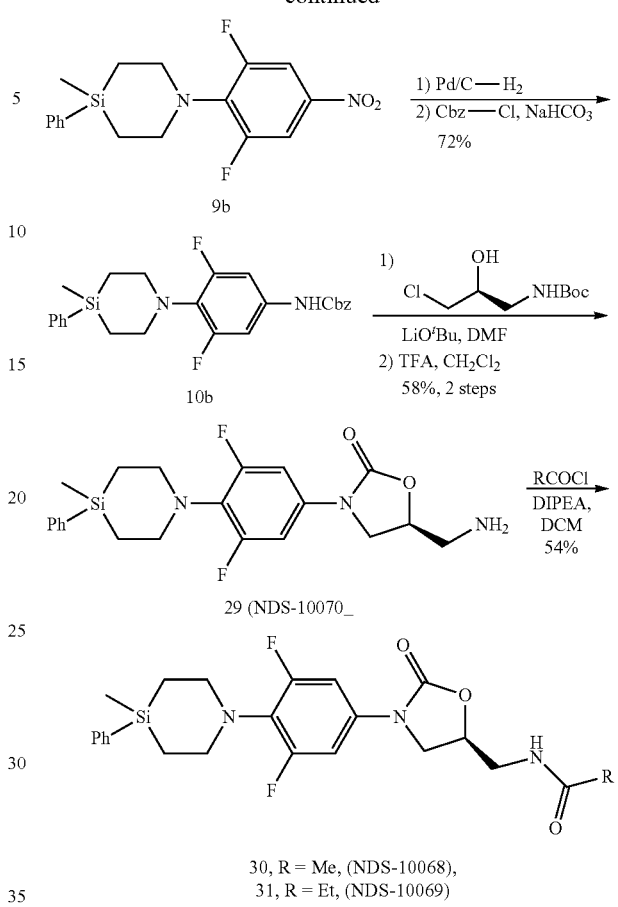

Preparation of 1-(2,6-difluoro-4-nitrophenyl)-4-methyl-4-phenyl-1,4-azasilinane (9b)

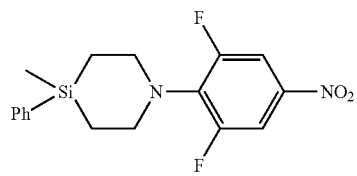 [SMILES: C[Si]1(c2ccccc2)CCN(c2c(F)cc([N+](=O)[O-])cc2F)CC1]

To a solution of 4,4-dimethyl-1,4-azasilinane hydrochloride 4 (1.45 g, 7.59 mmol) in EtOAc (15 mL), triethylamine (3.17 mL, 22.37 mmol) is added and stirred at 25° C. for 10 min. The reaction mixture is cooled to 0° C. and 1,2,3-trifluoro-5-nitrobenzene (0.8 mL, 6.8 mmol) is added drop wise and allowed to stir at 25° C. for 6 h. Water is then added and the organic layer is separated. The aqueous layer is extracted with EtOAc (2×10 mL) and the solvent is removed under reduced pressure. Column chromatography using hexane-EtOAc mixtures gives the product as a crystalline yellow solid 9b (1.96 g) in 83% yield.

$^1$H NMR (200 MHz, CDCl₃): δ 7.77-7.69 (m, 2H), 7.60-7.57 (m, 2H), 7.39-7.33 (m, 3H), 3.36 (t, J=6.0 Hz, 4H), 1.29-1.22 (m, 2H), 1.08-1.02 (m, 2H), 0.36 (s, 3H). $^{13}$C NMR (50 MHz, CDCl₃): δ 155.24 (dd, J=248.9 Hz, 8.2 Hz), 139.10 (t, J=11.5 Hz), 136.93, 136.60 (t), 133.84, 129.52, 128.11, 109.06 (dd, J=12.5 Hz, 17.5 Hz), 51.07, 13.99, −3.93. IR: 1606, 1515, 1335, 1216, 1110, 758 cm⁻¹.

Preparation of benzyl(3,5-difluoro-4-(4-methyl-4-phenyl-1,4-azasilinan-1-yl)phenyl)carbamate (10b)

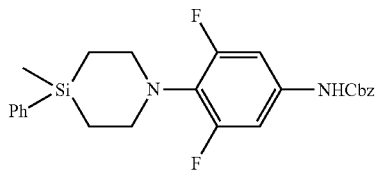 [SMILES: C[Si]1(c2ccccc2)CCN(c2c(F)cc(NC(=O)OCc3ccccc3)cc2F)CC1]

To a solution of 9b (1.96 g, 7.59 mmol) in THF, Pd/C is added for hydrogenation under a pressure of 35 psi in a par hydrogenator. The reaction mixture was filtered through celite. To the filtrate, saturated NaHCO₃ (1.90 g, 22.77 mmol) and CBzCl (1.3 mL, 9.10 mmol) were added and stirred at 25° C. for 5 h. The solvent is removed, 10 mL water is added and the aqueous layer is extracted with EtOAc. The crude mixture is then subjected to column chromatography on silica gel using hexane-DCM mixtures to afford the product 10b as a viscous liquid (1.80 g) in 71% yield.

¹H NMR (400 MHz, CDCl₃): δ 7.60-7.57 (m, 2H), 7.39-7.33 (m, 8H), 6.92 (d, J=10.0 Hz, 2H), 6.58 (s, 1H), 5.18 (s, 2H), 3.36 (t, J=6.0 Hz, 4H), 1.29-1.22 (m, 2H), 1.08-1.02 (m, 2H), 0.36 (s, 3H). ¹³C NMR (50 MHz, CDCl₃): δ 158.97 (dd, J=236.3, 9.8), 153.24, 138.00, 135.86, 133.97, 133.68 (t), 129.23, 128.70, 128.52, 128.39, 127.98, 126.24 (t, J=14.1 Hz), 102.82 (m), 67.30, 51.86, 14.38, −3.94. IR (CHCl₃): ν 3325, 2925, 2827, 1741, 1707, 1598, 1509, 1429, 1281, 1228, 985, 861, 730, 698 cm⁻¹.

Preparation of (S)-5-(aminomethyl)-3-(3,5-difluoro-4-(4-methyl-4-phenyl-1,4-azasilinan-1-yl)phenyl)oxazolidin-2-one (29): (NDS-10070)

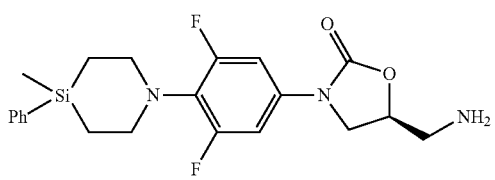 [SMILES: C[Si]1(c2ccccc2)CCN(c2c(F)cc(N3C[C@H](CN)OC3=O)cc2F)CC1]

To a solution of 10b (1.80 g, 3.98 mmol) and (S)-tert-butyl 3-chloro-2-hydroxypropylcarbamate (1.66 g, 7.96 mmol) in DMF (10 mL), LiOᵗBu (1.27 g, 15.92 mmol) is added at 0° C. The mixture is stirred at 25° C. for 45 h. The starting material 10b is not consumed completely. Saturated NH₄Cl is added; the organic phase is extracted with EtOAc (2×20 mL) and washed with brine solution, dried and concentrated. The crude residue is dissolved in 20 mL of DCM-TFA mixture (8:2) and stirred at 25° C. for 3 h. RM is concentrated and dissolved in water (10 mL), the aqueous layer is washed with diethyl ether (2×50 mL), basified with saturated NaHCO₃ and extracted with DCM (2×50 mL), and the DCM layer is dried and concentrated. The crude is purified by column chromatography on silica gel using hexane-EtOAc mixtures to obtain the product as an off-white solid (780 mg) in 65% (based on recovery of starting material) over 2 steps.

¹H NMR (200 MHz, CDCl₃): δ 7.61-7.57 (m, 2H), 7.40-7.37 (m, 3H), 7.17-7.01 (m, 2H), 4.73-4.60 (m, 1H), 3.97 (t, J=8.7 Hz, 1H), 3.78 (dd, J=8.5 Hz, 6.8 Hz, 1H), 3.38 (t, J=6.2 Hz, 4H), 3.03 (dq, J=13.6 Hz, 4.0 Hz, 2H), 1.26-0.99 (m, 4H), 0.36 (s, 3H). ¹³C NMR (50 MHz, CDCl₃): 158.6 (dd, J=246.6, 10.0 Hz), 154.4, 137.8, 133.9, 133.4 (t, J=13.9 Hz), 129.2, 127.9, 126.7 (t, J=14.6 Hz), 102.4-102.1 (m), 72.8, 62.6, 51.7, 46.2, 14.3, −4.0 IR (CHCl₃): ν 3423, 2931, 2833, 1709, 1635, 1514, 1265, 1111, 986, 863 cm⁻¹. M.P: 185-187° C.

ESI-MS: 440.13 (M+Na).

Preparation of (S)—N-((3-(3,5-difluoro-4-(4-methyl-4-phenyl-1,4-azasilinan-1-yl)phenyl)-2-oxooxazolidin-5-yl)methyl)acetamide (30) (NDS-10068)

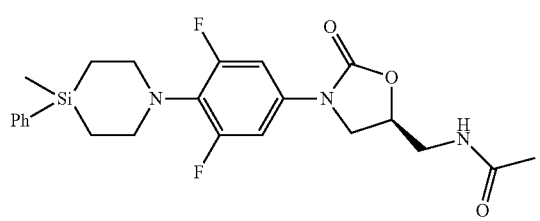 [SMILES: CC(=O)NC[C@H]1CN(c2cc(F)c(N3CC[Si](C)(c4ccccc4)CC3)c(F)c2)C(=O)O1]

To the solution of amine 29 (200 mg, 0.47 mmol) and DIPEA (0.16 mL, 0.95 mmol) in dry THF (4.0 mL), acetylchloride (0.04 mL, 0.57 mmol) is added at 0° C., and stirred at 25° C. for 3 h. Saturated NaHCO₃ (5.0 mL) is added to the reaction mixture and extracted with EtOAc (2×5 mL). The organic layer is washed with brine, dried and concentrated. The product is purified by column chromatography on silica gel using hexane-EtOAc mixtures to obtain the product as an off-white solid (120 mg) in 54% yield.

¹H NMR (200 MHz, CDCl₃): δ 7.61-7.57 (m, 2H), 7.40-7.37 (m, 3H), 7.13-6.98 (m, 2H), 6.08 (t, J=6.5 Hz, 1H), 4.83-4.71 (m, 1H), 3.98 (t, J=8.8 Hz, 1H), 3.74-3.56 (m, 3H), 3.38 (t, J=6.2 Hz, 4H), 2.03 (s, 3H), 1.34-0.99 (m, 4H), 0.36 (s, 3H). ¹³C NMR (50 MHz, CDCl₃): δ171.5, 159.74 (dd, J=245.9, 9.0), 154.3, 137.8, 133.7, 133.2 (t, J=13.2 Hz), 129.2, 127.9, 126.9 (t, J=14.2 Hz), 102.5 (m), 72.1, 51.7, 47.4, 41.8, 23.0, 14.3, −4.0. IR (CHCl₃): ν 3307, 2926, 1753, 1655, 1511, 1247, 1112, 862 cm⁻¹. M.P: 112-114° C. ESI-MS: 482.17 (M+Na).

Preparation of (S)—N-((3-(3,5-difluoro-4-(4-methyl-4-phenyl-1,4-azasilinan-1-yl)phenyl)-2-oxooxazolidin-5-yl)methyl)propionamide (31) (NDS-10069)

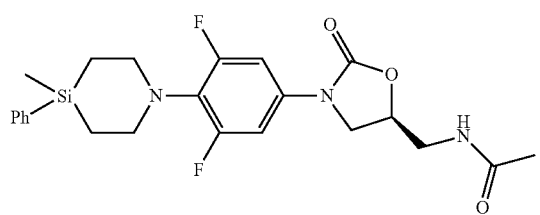 [SMILES: CC(=O)NC[C@H]1CN(c2cc(F)c(N3CC[Si](C)(c4ccccc4)CC3)c(F)c2)C(=O)O1]

To the solution of amine 29 (200 mg, 0.47 mmol) and DIPEA (0.16 mL, 0.95 mmol) in dry THF (4.0 mL), propionylchloride (0.05 mL, 0.57 mmol) is added at 0° C., and stirred at 25° C. for 3 h. Saturated NaHCO₃ (5.0 mL) is added to the reaction mixture and extracted with EtOAc (2×5 mL). The organic layer is washed with brine, dried and concentrated. The product is purified by column chromatography on silica gel using hexane-EtOAc mixtures to obtain the product as an off-white solid (125 mg) in 61% yield.

$^1$H NMR (200 MHz, CDCl$_3$): δ 7.61-7.57 (m, 2H), 7.40-7.37 (m, 3H), 7.13-6.98 (m, 2H), 5.97 (t, J=6.0 Hz, 1H), 4.82-4.70 (m, 1H), 3.98 (t, J=9.0 Hz, 1H), 3.76-3.62 (m, 3H), 3.38 (t, J=6.2 Hz, 4H), 2.24 (q, J=7.6 Hz, 2H), 1.34-0.99 (m, 7H), 0.36 (s, 3H). $^{13}$C NMR (50 MHz, CDCl$_3$): δ 175.2, 158.7 (dd, J=246.2, 9.1), 154.3, 137.8, 133.9, 133.2 (t, J=13.2 Hz), 129.2, 127.9, 126.9 (t, J=14.3 Hz), 102.5 (m), 72.1, 51.7, 47.5, 41.8, 29.4, 14.3, 9.8, −4.0. IR (CHCl$_3$): ν 3265, 3069, 2926, 1740, 1649, 1510, 1449, 1426, 1245, 757 cm$^{-1}$. M.P: 123-125° C. ESI-MS: 496.20 (M+Na).

Scheme 9

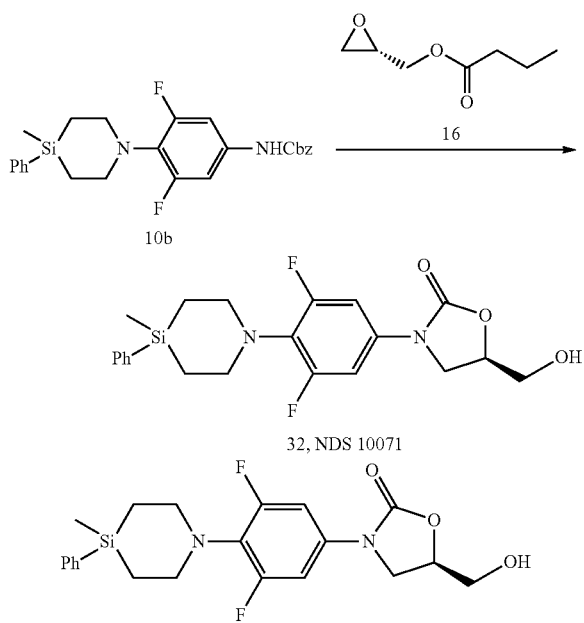

Preparation of (R)-3-(3,5-difluoro-4-(4-methyl-4-phenyl-1,4-azasilinan-1-yl)phenyl)-5-(hydroxyl methyl)oxazolidin-2-one (32) (NDS-10071)

To the Cbz compound 10b (180 mg, 0.25 mmol) in dry THF (5 mL) at −78° C., n-BuLi 2.0 M (0.21 mL, 0.42 mmol) is added and stirred for 30 min. Further, glycidylbutyrate 16 (0.06 mL, 0.42 mmol) is added drop wise at −78° C., and allowed to stir at 25° C. for overnight. RM is quenched with saturated NH$_4$Cl (5 mL) and extracted with EtOAc (2×10 mL). The organic layer is washed with brine (5 mL), dried and concentrated. The product is purified by column chromatography on silica gel using hexane-EtOAc mixtures to obtain the product as an off-white solid (75 mg) in 46% yield.

$^1$H NMR (400 MHz, CDCl$_3$): δ 7.61-7.56 (m, 2H), 7.40-7.37 (m, 3H), 7.16-7.01 (m, 2H), 4.79-4.68 (m, 1H), 4.03-3.70 (m, 4H), 2.17 (bs, 1H), 3.38 (t, J=6.2 Hz, 4H), 1.34-0.99 (m, 4H), 0.36 (s, 3H). $^{13}$C NMR (100 MHz, CDCl$_3$): 158.6 (dd, J=246.6, 10.0 Hz), 154.4, 137.8, 133.9, 133.4 (t, J=13.9 Hz), 129.2, 127.9, 126.7 (t, J=14.6 Hz), 102.4-102.1 (m), 72.8, 62.6, 51.7, 46.2, 14.3, −4.0 IR (CHCl$_3$): ν 3423, 2931, 2833, 1709, 1635, 1514, 1265, 1111, 986, 863 cm$^{-1}$. M.P: 105-107° C. ESI-MS: 441.10 (M+Na).

Preparation of (S)-tert-butyl((3-(4-(4,4-dimethyl-1,4-azasilinan-1-yl)-3,5-difluorophenyl)-2-oxooxazolidin-5-yl)methyl)carbamate (33) (NDS-10031)

$^1$H NMR (400 MHz, CDCl$_3$): δ7.08-7.02 (m, 2H), 4.98 (bs, 1H), 4.74-4.71 (m, 1H), 3.96 (t, J=8.8 Hz, 1H), 3.77 (t, J=8.0 Hz, 1H), 3.50 (m, 2H), 3.29 (t, J=6.0 Hz, 4H), 1.41 (s, 9H), 0.87 (t, J=6.0 Hz, 4H), 0.10 (s, 6H). $^{13}$C NMR (100 MHz, CDCl$_3$): 158.7 (246.6, 9.3), 156.3, 154.1, 133.3 (13.8) 127.0, 102.0, 801.3, 71.9, 51.8, 47.2, 28.2, 15.5, −3.0 IR (CHCl$_3$): ν 3265, 3069, 2926, 1740, 1649, 1510, 1449, 1426, 1245, 757 cm$^{-1}$. ESI-MS: 478.10 (M+Na).

Selected Compounds with Antibacterial Activity Against Various Strains

TABLE 1

| Compound no./ Organism | NDS-10024 (12) | NDS-10026 12r | NDS-10028 (23) | NDS-10031 33 | NDS-10033 (13) | NDS-10052 (27) | NDS-10053 (25) | NDS-10054 (22) | NDS-10056 (24) |
|---|---|---|---|---|---|---|---|---|---|
| S.aureus ATCC13709 Smith | 16 | >16 | 8 | >16 | 32 | >32 | 16 | 16 | >32 |
| S.aureus ATCC 29213 | 16 | 16 | >16 | >16 | 32 | >32 | 16 | 16 | >32 |
| MRSA ATCC 43300 | 16 | 32 | >32 | nt | 32 | >32 | 16 | 16 | 16 |
| MRSA 562 | 16 | 16 | 8 | >16 | 32 | 16 | 16 | 16 | 8 |
| S.aureus 2 (PVL + ve) | 16 | 32 | >32 | nt | 32 | >32 | 16 | 16 | 8 |
| S.aureus ATCC Newman 25904 | 16 | 32 | >32 | nt | 32 | >32 | 16 | 16 | 16 |
| MRSA ATCC BAA 39 | 16 | 16 | 8 | >16 | 16 | 16 | 8 | 16 | 32 |
| S.aureus DB00026 | 16 | 32 | >32 | nt | 32 | 32 | 16 | 16 | >32 |
| MRSA 252 BAA 1720 | 16 | 32 | >32 | nt | 32 | >32 | 8 | 16 | 32 |
| S.epidermidis ATCC 14990 | 8 | 16 | 4 | >16 | 8 | 16 | 8 | 16 | 16 |
| MRSE ATCC 35984 | 8 | 16 | 8 | >16 | 16 | 32 | 8 | 16 | 32 |
| E.faecalis ATCC 29212 | 16 | >16 | 8 | >16 | 32 | >32 | 32 | 16 | 32 |
| E.faecalis ATCC 51299(VRE&HLAR) | 16 | 16 | 8 | >16 | 16 | >32 | 16 | 16 | 8 |
| E.faecalis ATCC 19433 | 16 | >16 | 16 | >16 | 32 | >32 | 32 | 16 | 32 |
| E.faecium ATCC 19434 | 16 | >16 | 8 | >16 | 16 | 16 | 16 | 16 | 32 |
| E.faecium ATCC49224 | 8 | 8 | 8 | nt | 8 | 8 | 32 | 16 | 32 |
| E.faecium ATCC 35667 | 8 | 8 | 8 | nt | 16 | 32 | 8 | 8 | 32 |

TABLE 1-continued

| Compound no./Organism | NDS-10024 (12) | NDS-10026 12r | NDS-10028 (23) | NDS-10031 33 | NDS-10033 (13) | NDS-10052 (27) | NDS-10053 (25) | NDS-10054 (22) | NDS-10056 (24) |
|---|---|---|---|---|---|---|---|---|---|
| E.coli 7632 | >32 | >32 | >32 | >32 | >32 | >32 | >32 | >32 | >32 |
| S.aureus FDA 209P | 8 | 16 | 8 | >16 | 16 | 16 | 8 | 16 | 8 |
| S.aureus ATCC 49775 PVL + ve | 16 | >16 | 16 | >16 | 32 | >32 | 16 | 16 | 32 |
| S.aureus ATCC 700699 Mu50 | 8 | 16 | 8 | >16 | 16 | 8 | 8 | 16 | 16 |
| MRSA 0-2657 | 8 | 16 | 8 | >16 | 16 | >32 | 8 | 16 | 16 |
| MRSA DB 00026 | 16 | >16 | 8 | >16 | 32 | >32 | 32 | 16 | 32 |
| S.aureus 13709 LNZ mutant | >16 | >16 | >16 | >16 | >32 | >32 | >32 | 32 | >32 |
| S.epidermidis ATCC 12228 | 8 | 16 | 4 | >16 | 8 | >32 | 8 | 32 | 8 |
| MRSE ATCC 35983 | 8 | 16 | 4 | >16 | 16 | >32 | 32 | 32 | 32 |
| S.epidermis St 358 | 8 | >16 | 8 | >16 | 16 | >32 | 16 | 16 | 32 |
| E.faecalis SP 346 VRE | 16 | >16 | 8 | >16 | 32 | >32 | 32 | 16 | 16 |
| E.faecium 6A VRE | 16 | 16 | 4 | >16 | 16 | 8 | 4 | 8 | 8 |
| E.faecium 134 VRE | 16 | >16 | 8 | >16 | 32 | >32 | 32 | 16 | 32 |
| E.faecium 06076 VRE | 16 | >16 | 8 | >16 | 32 | >32 | >32 | 16 | >32 |
| E.faecium ATCC 3567 | 16 | >16 | 16 | >16 | 16 | 32 | 16 | 8 | 32 |

Selected Compounds with Antibacterial Activity Against Various Strains

TABLE 2

| Compound no./Organism | NDS-10057 (11) | NDS-10058 (28) | NDS-10059 (17) | NDS-10060 (21) | NDS-10061 (14) | NDS-10062 (15) | NDS-10070 (29) | NDS-10071 (32) | Linezolid |
|---|---|---|---|---|---|---|---|---|---|
| S.aureus ATCC 13709 Smith | >32 | >32 | >32 | 16 | 8 | 4 | >32 | 32 | 2 |
| S.aureus ATCC 29213 | >32 | >32 | >32 | 32 | 16 | 4 | >32 | >32 | 2 |
| MRSA ATCC 43300 | >32 | >32 | >32 | 32 | >32 | 4 | >32 | >32 | 4 |
| MRSA 562 | >32 | >32 | >32 | 16 | 16 | 4 | 32 | 32 | 2 |
| S.aureus2 (PVL + ve) | >32 | 32 | >32 | 16 | 16 | 4 | >32 | 32 | 2 |
| S.aureus ATCC Newman 25904 | >32 | 32 | >32 | 16 | 16 | 4 | >32 | 16 | 2 |
| MRSA ATCC BAA 39 | >32 | >32 | >32 | 16 | 16 | 4 | >32 | 32 | 2 |
| S.aureus DB00026 | >32 | >32 | >32 | 16 | 8 | 4 | >32 | 32 | 1 |
| MRSA 252 BAA 1720 | >32 | >32 | >32 | 32 | 16 | 8 | >32 | 32 | 1 |
| S.epidermidis ATCC 14990 | >32 | >32 | 32 | 8 | 8 | 4 | >32 | 16 | 2 |
| MRSE ATCC 35984 | 32 | 32 | 32 | 16 | 8 | 2 | 32 | 16 | 1 |
| E.faecalis ATCC 29212 | >32 | 32 | 32 | 8 | 8 | 1 | 32 | 8 | 0.5 |
| E.faecalis ATCC 51299(VRE&HLAR) | 16 | 32 | 32 | 16 | 32 | 4 | 32 | 32 | 1 |
| E.faecalis ATCC 19433 | 32 | 32 | >32 | 16 | 16 | 2 | 32 | 16 | 1 |
| E.faecium ATCC 19434 | 32 | 32 | 32 | 32 | 32 | 8 | 32 | 32 | 2 |
| E.faecium ATCC 49224 | 32 | >32 | >32 | 32 | 16 | 4 | 32 | 32 | 2 |
| E.faecium ATCC 35667 | 32 | >32 | >32 | 32 | 16 | 4 | 32 | 16 | 4 |
| E. coli 7632 | 32 | 16 | 32 | 16 | 8 | 2 | 32 | 16 | 1 |
| S.aureus FDA 209P | >32 | >32 | >32 | >32 | >32 | >32 | >32 | >32 | >32 |
| S.aureus ATCC 49775 PVL + ve | >32 | 32 | 32 | 16 | 16 | 4 | >32 | 16(ppt) | 2 |
| S.aureus ATCC 700699 Mu50 | >32 | >32 | >32 | 32 | 32 | 8 | >32 | 32 | 2 |
| MRSA 0-2657 | >32 | >32 | 32 | 16 | 16 | 4 | >32 | 8(ppt) | 1 |
| MRSA DB 00026 | >32 | >32 | >32 | 16 | 16 | 4 | >32 | 16 | 2 |
| S.aureus 13709 LNZ mutant | >32 | 32 | >32 | 32 | 32 | 4 | >32 | 16(ppt) | 2 |
| S.epidermidis ATCC 12228 | >32 | >32 | >32 | >32 | >32 | >32 | >32 | >32 | >16 |
| MRSE ATCC 35983 | >32 | 16 | >32 | 32 | 16 | 4 | >32 | 16 | 1 |
| S.epidermis St 358 | >32 | 32 | 32 | 16 | 32 | 4 | >32 | 16 | 2 |

TABLE 2-continued

| Compound no./Organism | NDS-10057 (11) | NDS-10058 (28) | NDS-10059 (17) | NDS-10060 (21) | NDS-10061 (14) | NDS-10062 (15) | NDS-10070 (29) | NDS-10071 (32) | Linezolid |
|---|---|---|---|---|---|---|---|---|---|
| E.faecalis SP 346 VRE | >32 | 32 | 32 | 16 | 16 | 4 | >32 | 16(ppt) | 2 |
| E.faecium 6A VRE | >32 | 16 | >32 | 32 | 32 | 8 | >32 | 32 | 2 |
| E.faecium 134 VRE | 32 | 4 | 32 | 16 | 16 | 4 | >32 | 8 | 2 |
| E.faecium 06076 VRE | >32 | 32 | >32 | 32 | 32 | 4 | >32 | 32 | 2 |
| E.faecium ATCC 3567 | >32 | >32 | >32 | >32 | 32 | 4 | >32 | >32 | 2 |

The strains in the MIC panel are either from ATCC or clinical isolates in the RCI culture collection.

MIC procedure (minimum inhibitory concentration) of NCEs by microbroth dilution method against facultative bacteria: As per CLSI guidelines M7-A7 Minimum inhibitory concentration (MIC) has been an indicator of in vitro antibacterial activity.

Method:
Microbroth dilution method
Medium:
1. Cation adjusted Mueller Hinton II Broth (MHB-BD)): staphylococci spp., enterococci spp.

Preparation of Compounds:
1 mg/mL of stock solution of compounds and standard drugs are prepared in dimethylsulfoxide/distilled water/solvent and further 2 fold dilutions are done in 96 well U bottom microtiter plates as per CLSI guidelines.

Inoculum Preparation:
Saline suspensions are prepared from three-four isolated bacterial colonies taken from cultures grown on TSA (Tryptic Soya Agar) for 18-24 h.

The turbidity of the suspension is adjusted to 0.5McFarland standard (~1.5×10$^8$ CFU/mL). Cultures are diluted 100 times in MHB and 50 µl of diluted culture broth is added in wells already containing 50 µl of broth containing diluted compounds and growth well (positive control) to get approximately 3-7×10$^5$ CFU/ml. Cultures are randomly selected for CFU determination of inoculum suspensions. Micro titer plates are then incubated overnight at 35-37° C. in ambient air BOD.

End Point Determination of MIC:
MIC is recorded as the micro dilution well with lowest concentration of the drug at which there is complete disappearance of growth of the organism in comparison to positive control (growth well) as detected by the unaided eye.

Quality Control Strains
*Staphylococcus aureus* ATCC 29213
*Enterococcus faecalis* ATCC 29212

REFERENCES

1. Clinical and Laboratory Standards Institute, Methods for Dilution Antimicrobial Susceptibility Tests for Bacteria That Grow Aerobically; Approved Standard—Seventh Edition. M7-A7, Vol. 26. No. 2 (January 2006)
2) Clinical and Laboratory Standards Institute, Performance Standards for Antimicrobial Susceptibility Testing—Sixteenth informational supplement, M100-S17, Vol. 27 No. 1, January 2007

From the above tables 1 and 2, it is evident that some of the compounds according to the invention have shown good efficacy with low MIC against particularly *S. epidermidis* ATCC 12228; *S. aureus* FDA 209P over Linezolid, where, Linezolid shows the requirement of higher values of MIC. Therefore, the compounds of the invention are specifically effective against a wide variety of gram-positive pathogens including those resistant to methicillin and vancomycin. Also, the compounds of the invention are useful in treating bacterial infections that are resistant to Linezolid. Thus the compounds of the invention are effective in treating variety of bacterial infections in animals. The animal according to the invention is a mammal, particularly, the mammal is human.

Anti-TB Activity[a] of Selected Compounds

MIC values of various antibiotics against $H_{37}Rv$ is determined in 7H9-OADC media supplemented with 0.5% Glycerol and 1 mg/ml Tryptone at 37° C. in 96-well microtiter plates using the colorimetric resazurinmicrotiter assay, and growth is measured by visual readout. Rifampicin is used as a positive drug control. The activities are shown in below table 3.

TABLE 3

| Compound | MIC[b] (µg/ml) |
|---|---|
| NDS-10024(12) | 6.25 |
| NDS-10026 | 50 |
| NDS-10028(23) | >50 |
| NDS-10053(25) | 50 |
| NDS-10054(22) | 25 |
| NDS-10055(26) | >100 |
| NDS-10056(24) | 50 |
| NDS-10057(11) | 25 |
| NDS-10058(28) | 12.5 |
| NDS-10059(17) | 100 |
| NDS-10060(21) | 50 |
| NDS-10061(14) | 25 |
| NDS-10062(15) | 50 |
| NDS-10068(30) | >100 |
| NDS-10069(31) | 50 |
| NDS-10070(29) | 50 |
| NDS-10071(32) | 50 |
| Rifampicin | 0.3 | a. Through inhibition of *Mycobacterium tuberculosis* $H_{37}Rv$ growth.
[b] Minimum Inhibitory Concentration (90%).

From the above table, it is evident that selective compounds such as NDS-10024 as well as NDS-10058 have been found to show good anti-tubercular activity and hence can effectively be used for the treatment of tuberculosis.

The invention claimed is:

1. Sila analogs of oxazolidinone derivatives of formula I or an enantiomer, diastereomer, racemate, tautomer, geometrical isomer, dimer, solvate, hydrate or pharmaceutically acceptable salt thereof

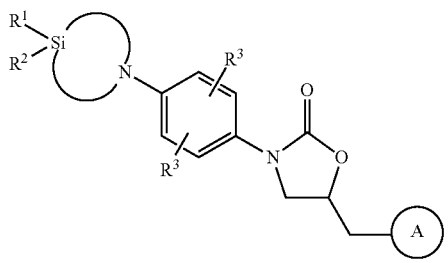

Formula-I wherein, $R^1$ and $R^2$ each are individually selected from C1 to C12 alkyl, aryl, heteroaryl, aralkyl or $R^1$ and $R^2$ may form 4-8 membered alicyclic or aromatic ring with additionally containing hetero atom;

$R^3$ is selected from hydrogen, chloro, fluoro, nitro, cyano, amino, C1-C8 alkyl amino, C1-C8 dialkyl amino, C1-C8 alkoxy, p-toluenesulfonyl, $CONH_2$, NHCOR, COOH, $CF_3$, hydroxy, OCOR, alkyl(optionally substituted with chloro, fluoro, hydroxy, C1-C8 alkoxy, amino, C1-C8 alkylamino, or C1-C8 dialkylamino), aryl, hetero aryl, aralkyl;

"A" is independently selected from the group consisting of;

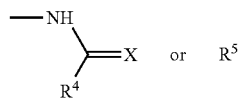

wherein, $R^4$ is selected from hydrogen, (C1-C8) alkyl optionally substituted with chloro, fluoro, hydroxy, C1-C8 alkoxy, amino, C1-C8 alkylamino, or C1-C8 dialkylamino, aryl, hetero aryl, or aralkyl;

X is selected from O, S, NH, or N—OR';

R' is selected from C1 to C12 alkyl, aryl, heteroaryl, aralkyl;

$R^5$ is selected from hydrogen, hydroxyl, (C1-C4) alkyl, alkyl optionally substituted with chloro, fluoro, hydroxyl, C1-C8 alkoxy, amino, C1-C8 alkylamino, or C1-C8 dialkylamino, aryl, hetero aryl, aralkyl; p-toluenesulfonyl, methanesulfony, $N_3$; and each arch between Si and N is —$CH_2$—$CH_2$—.

2. Sila analogs of oxazolidinone derivatives of formula I according to claim 1, comprises
(S)—N-((3-(4-(4,4-dimethyl-1,4-azasilinan-1-yl)-3-fluorophenyl)-2-oxooxazolidin-5-yl)methyl)acetamide (12): (NDS 10024)
(S)-5-(aminomethyl)-3-(4-(4,4-dimethyl-1,4-azasilinan-1-yl)-3-fluorophenyl)oxazolidin-2-one(11): (NDS-10057)
(S)—N-((3-(4-(4,4-dimethyl-1,4-azasilinan-1-yl)-3-fluorophenyl)-2-oxooxazolidin-5-yl)ethyl)propionamide (13): (NDS 10033)
(S)-methyl((3-(4-(4,4-dimethyl-1,4-azasilinan-1-yl)-3-fluorophenyl)-2-oxooxazolidin-5-yl)methyl)carbamate ((14): (NDS-10061)
(S)—O-methyl((3-(4-(4,4-dimethyl-1,4-azasilinan-1-yl)-3-fluorophenyl)-2-oxooxazolidin-5-yl)methyl)carbamothioate (15): (NDS-10062)
(R)-3-(4-(4,4-dimethyl-1,4-azasilinan-1-yl)-3-fluorophenyl)-5-(hydroxymethyl)oxazolidin-2-one ((17): (NDS-10059)
(R)-(3-(4-(4,4-dimethyl-1,4-azasilinan-1-yl)-3-fluorophenyl)-2-oxooxazolidin-5-yl)methyl methanesulfonate (18)
(R)-5-(azidomethyl)-3-(4-(4,4-dimethyl-1,4-azasilinan-1-yl)-3-fluorophenyl)oxazolidin-2-one (19)
(R)-5-((1H-1,2,3-triazol-1-yl)methyl)-3-(4-(4,4-dimethyl-1,4-azasilinan-1-yl)-3-fluorophenyl)oxazolidin-2-one ((21)(NDS-10060)
(S)-5-(aminomethyl)-3-(4-(4,4-dimethyl-1,4-azasilinan-1-yl)-3,5-difluorophenyl)oxazolidin-2-one ((22): (NDS-10054)
(S)—N-((3-(4-(4,4-dimethyl-1,4-azasilinan-1-yl)-3,5-difluorophenyl)-2-oxooxazolidin-5-yl)methyl)acetamide ((23): (NDS-10028)
(S)—N-((3-(4-(4,4-dimethyl-1,4-azasilinan-1-yl)-3,5-difluorophenyl)-2-oxooxazolidin-5-yl)methyl)propionamide ((24): (NDS-10056)
(S)-methyl(3-(4-(4,4-dimethyl-1,4-azasilinan-1-yl)-3,5-difluorophenyl)-2-oxooxazolidin-5-yl)methylcarbamate ((25): (NDS-10053)
(S)—O-methyl(3-(4-(4,4-dimethyl-1,4-azasilinan-1-yl)-3,5-difluorophenyl)-2-oxooxazolidin-5-yl)methylcarbamothioate ((26): (NDS-10055)
(R)-3-(4-(4,4-dimethyl-1,4-azasilinan-1-yl)-3,5-difluorophenyl)-5-(hydroxymethyl)oxazolidin-2-one (27): (NDS-10052)
(R)-5-((1H-1,2,3-triazol-1-yl)methyl)-3-(4-(4,4-dimethyl-1,4-azasilinan-1-yl)-3,5-difluorophenyl)oxazolidin-2-one ((28): (NDS-10058)
(S)-5-(aminomethyl)-3-(3,5-difluoro-4-(4-methyl-4-phenyl-1,4-azasilinan-1-yl)phenyl)oxazolidin-2-one ((29): (NDS-10070)
(S)—N-((3-(3,5-difluoro-4-(4-methyl-4-phenyl-1,4-azasilinan-1-yl)phenyl)-2-oxooxazolidin-5-yl)methyl)acetamide (30): (NDS-10068)
(S)—N-((3-(3,5-difluoro-4-(4-methyl-4-phenyl-1,4-azasilinan-1-yl)phenyl)-2-oxooxazolidin-5-yl)methyl)propionamide (31): (NDS-10069)
(R)-3-(3,5-difluoro-4-(4-methyl-4-phenyl-1,4-azasilinan-1-yl)phenyl)-5-(hydroxymethyl)oxazolidin-2-one (32): (NDS-10071).

3. A compound as claimed in claim 1 wherein the said compound is found to have antibacterial activity against strains of S.aureus, S.epidermidis, E.faecalis, E.faecium and E. coli.

4. A compound as claimed in claim 1 wherein the said compound is found to have anti tubercular activity against strain of Mycobacterium tuberculosis $H_{37}Rv$.

5. A process for the preparation of sila analogs of oxazolidine derivatives of formula I comprising of
(i) reacting 1,4-azasilinane hydrochloride compound of general formula (a)

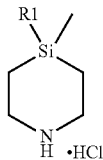

General Formula (a)

wherein R1 is alkyl or phenyl with fluronitrophenyl in presence of triethylamine in ethyl acetate at a temperature ranging between 20-45° C. to obtain N-aryl-1,4-azasilinane compound of general formula (b) wherein R1 is alkyl or phenyl, one or two R2 wherein R2 is F or H General Formula (b)

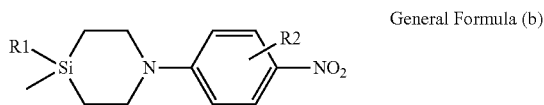

(ii) reacting compound (b) with H₂-Pd/C in THF at a pressure of 35-50psi to obtain an amino compound, filtrating the reaction mixture through celite, followed by addition of CBzCl to the filtrate and stirring for 5 hours at room temperature to obtain compound of general formula (c) Benzyl 4-(4,4-dimethyl-1,4-azasilinan-1-yl)-3-fluorophenylcarbamate wherein R1 is alkyl or phenyl, wherein R2 is F or H General Formula (c)

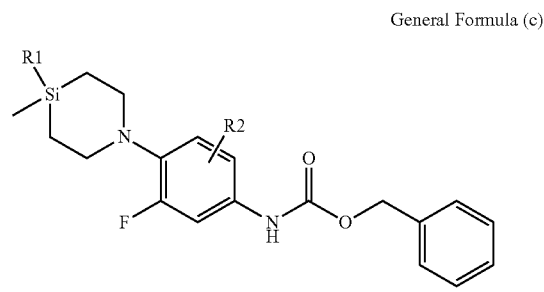

(iii) reacting compound (c) with (S)-tert-butyl 3-chloro-2-hydroxypropylcarbamate in LiO'Bu at a temperature in the range of 0° C. to 25° C. to obtain compound of general formula (d) (S)-5-(aminomethyl)-3-(4-(4,4-dimethyl-1,4-azasilinan-1-yl)-3-fluorophenyl)oxazolidin-2-one wherein R1 is alkyl or phenyl, wherein R2 is F or H General formula (d)

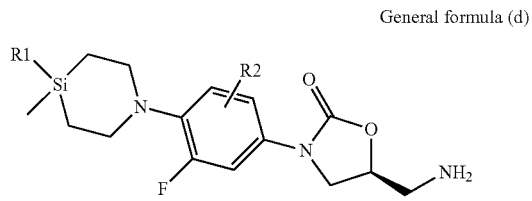

(iv) reacting compound (d) with acid chloride of formula RCOCl wherein R is alkyl and N,N-diisopropylethylamine (DIPEA) to obtain corresponding amide compounds,

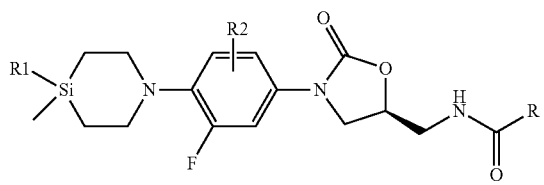

(v) converting compound (d) to corresponding ester of compound 14 (S)-methyl((3-(4-(4,4-dimethyl-1,4-azasilinan-1-yl)-3-fluorophenyl)-2-oxooxazolidin-5-yl)methyl)carbamate by reacting with CDI and trimethylamine in the presence of methanol (vi) converting compound (d) to compound of formula 15 (S)—O-methyl((3-(4-(4,4-dimethyl-1,4-azasilinan-1-yl)-3-fluorophenyl)-2-oxooxazolidin-5-yl)methyl)carbamothioate by reacting with CSCl₂ in the presence of methanol to obtain compound of formula 15.

6. A process for the preparation of compound 17 to 21 (Scheme 4) wherein the process steps comprises of the following steps:—
   i. reacting compound of general formula (c) with compound 16 glycidylbutyrate in the presence of n-BuLi in THF at a temperature of about 25° C. to obtain compound of formula 17 (R)-3-(4-(4,4-dimethyl-1,4-azasilinan-1-yl)-3-fluorophenyl)-5-(hydroxymethyl)oxazolidin-2-one Formula-17

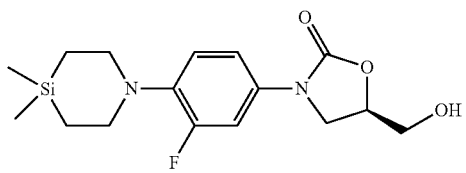

ii. converting the hydroxycompound 17 to corresponding misilate by reacting with Methanesulfonylchloride in the presence of trimethylamine followed by diazotization to produce azido compound of formula 19 (R)-5-(azidomethyl)-3-(4-(4,4-dimethyl-1,4-azasilinan-1-yl)-3-fluorophenyl)oxazolidin-2-one Formula-19

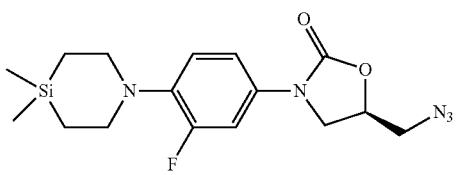

iii. reacting azido compound 19 with bicyclodiene under reflux temperature to produce compound of formula 21 (R)-5-((1H-1,2,3-triazol-1-yl)methyl)-3-(4-(4,4-dimethyl-1,4-azasilinan-1-yl)-3-fluorophenyl)oxazolidin-2-one Formula-21

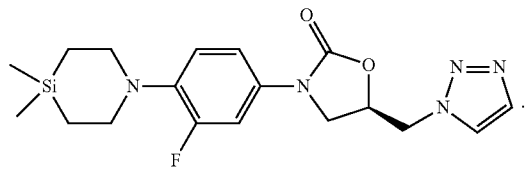

7. A pharmaceutical composition comprising compounds of formula I according to claim 1 optionally along with one or more pharmaceutical excipients.

8. The pharmaceutical composition according to claim 6, wherein said compositions optionally comprise one or more suitable anti-bacterial drugs such as vancomycin, doxycycline, penicillin, clindamycin, gentamicin, rifampicin etc. to provide synergistic effect on treatment regimen.

\* \* \* \* \*